United States Patent [19]

Doria et al.

[11] Patent Number: 4,598,090

[45] Date of Patent: Jul. 1, 1986

[54] CONDENSED BENZOPYRONE DERIVATIVES

[75] Inventors: Gianfederico Doria, Milan; Carlo Passarotti, Gallarate; Ada Buttinoni, Milan, all of Italy

[73] Assignee: Farmitalia Carlo Erba, S.p.A., Milan, Italy

[21] Appl. No.: 592,472

[22] Filed: Mar. 22, 1984

[30] Foreign Application Priority Data

Apr. 6, 1983 [GB] United Kingdom ................ 8309260

[51] Int. Cl.$^4$ ..................... A61K 31/35; C07D 311/82
[52] U.S. Cl. .................................. 514/455; 549/395; 549/59; 544/150; 546/269; 546/196; 548/250; 548/525
[58] Field of Search .......................... 549/395; 514/455

[56] References Cited

PUBLICATIONS

S. Zafaruddin Ahmad and R. D. Desai., Heterocyclic Compounds, III, Chemical Abstracts, vol. 32, pp. 559–560, (1957).

Yates, Peter; Bichan, David J.; McCloskey, J. Edmund, 101334g, Condensation of 1,3-Cyclohexanediones, etc., Chemical Abstracts, vol. 77, 1972, p. 404.

Untze, W. (Landesanst. Lebensm.-, etc., 126235e, New Antioxidants and Their Properties, 27-Heterocycles-vol. 79, 1973, p. 126224.

Porshnev, Yu. N.; Churkina, V. A.; Titov, V. V. (Navchno-Issled. etc.), 90:72006n, Synthesis of Styryl-Substituted 2-Phenyl- and 1,2-Diphenylcyclopenta(b)-Chromenes; 27-Heterocycles, vol. 90, 1979., p. 72012.

*Primary Examiner*—Ethel G. Love
*Attorney, Agent, or Firm*—Murray and Whisenhunt

[57] ABSTRACT

The present invention relates to new condensed benzopyrone derivatives, to a process for their preparation and to pharmaceutical compositions containing them.

5 Claims, No Drawings

CONDENSED BENZOPYRONE DERIVATIVES

The invention provides compounds having the following general formula (I)

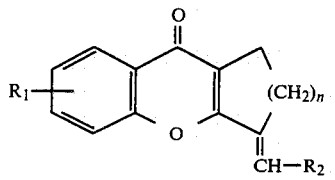
(I)

wherein
n is 1 or 2;
$R_1$ is
(a) hydrogen, halogen or $C_1$-$C_6$ alkyl;
(b) cyano, aminocarbonyl, 5-tetrazolyl, carboxy or a $C_1$-$C_6$ alkoxycarbonyl group unsubstituted or substituted by a di($C_1$-$C_6$)alkylamino group;
(c) nitro, amino, morpholino, piperidino or N-pyrrolidinyl;
(d) a

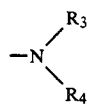

group, wherein $R_3$ is hydrogen or $C_1$-$C_6$ alkyl and $R_4$ is:
(a') formyl, $C_2$-$C_6$ alkanoyl or $C_1$-$C_6$ alkyl, wherein the alkyl is unsubstituted or substituted by one or two substituents chosen from hydroxy and phenyl;
(b') a —(CO)$_m$—A—$R_5$ group, wherein m is zero or 1; A completes a single bond, or is a phenylene moiety, or it is a branched or straight $C_1$-$C_6$ alkylene or $C_2$-$C_6$ alkenylene chain and $R_5$ is:
(a") carboxy or $C_1$-$C_6$ alkoxycarbonyl, unsubstituted or substituted by a di-($C_1$-$C_6$)alkylamino group; or
(b") halomethyl or

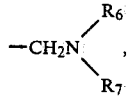

wherein each of $R_6$ and $R_7$ is independently hydrogen or $C_1$-$C_6$ alkyl or $R_6$ and $R_7$, taken together with the nitrogen atom to which they are linked, form a heterocyclic ring chosen from N-pyrrolidinyl, N-piperazinyl, piperidino and morpholino, wherein the N-piperazinyl ring is unsubstituted or substituted by $C_1$-$C_6$ alkyl, phenyl or by pyridyl, the piperidino ring is unsubstituted or substituted by one or two $C_1$-$C_6$ alkyl groups, and the morpholino ring is unsubstituted or substituted by methyl;
(e) hydroxy or a —OR$_4$ group, wherein $R_4$ is as defined above;
$R_2$ represents a thienyl, a furyl or a pyridyl group, wherein each of these groups is unsubstituted or substituted by a $C_1$-$C_3$ alkyl group, or $R_2$ is a group of formula

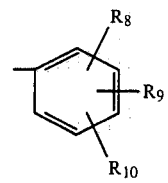

wherein each of $R_8$, $R_9$ and $R_{10}$ is independently hydrogen; halogen; $C_1$-$C_6$ alkyl; hydroxy; $C_1$-$C_6$ alkoxy; $C_3$-$C_4$ alkenyloxy; formyloxy; $C_2$-$C_6$ alkanoyloxy; carboxy; $C_1$-$C_6$ alkoxycarbonyl; nitro; or a group

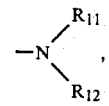

wherein each of $R_{11}$ and $R_{12}$ independently represents hydrogen, $C_1$-$C_6$ alkyl, formyl or $C_2$-$C_6$ alkanoyl; or any two adjacent $R_8$, $R_9$ and $R_{10}$ groups, taken together, form a $C_1$-$C_3$ alkylenedioxy group, and the pharmaceutically acceptable salts thereof, and wherein, when n is 1 and, at the same time, $R_2$ is unsubstituted phenyl, $R_1$ is other then hydrogen.

The scope of this invention includes also all the possible isomers of the compounds of formula (I) (e.g. Z and E isomers and optical isomers) and the mixture thereof. The numbering used to identify the position of the substituents in the compounds of formula (I) is the following one:

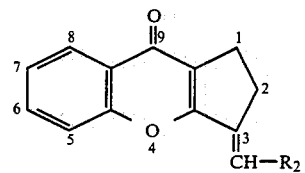

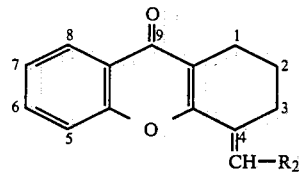

$R_1$ may be on the $C_5$ or $C_6$ or $C_7$ or $C_8$ carbon atom, preferably it is on the $C_6$ or $C_7$ carbon atom.

The alkyl, alkylene, alkenylene, alkylamino, alkoxycarbonyl, alkoxy, alkenyloxy, alkanoyl and alkanoyloxy groups may be branched or straight chain groups.

A $C_1$-$C_6$ alkyl group is preferably a $C_1$-$C_4$ alkyl group, in particular methyl, ethyl, propyl and isopropyl.

A halogen atom is, for example, fluorine, chlorine and bromine, preferably it is fluorine and chlorine.

A halomethyl group is preferably chloromethyl and bromomethyl.

A $C_1$-$C_6$ alkoxycarbonyl group, is preferably a $C_1$-$C_4$ alkoxycarbonyl group, in particular, methoxycarbonyl and ethoxycarbonyl.

A C$_2$–C$_6$ alkanoyl group is, for example, acetyl, propionyl, butyryl, valeryl and isovaleryl, preferably acetyl.

A C$_1$–C$_6$ alkoxy group is for example a C$_1$–C$_4$ alkoxy group, in particular methoxy and ethoxy.

A C$_1$–C$_3$ alkylenedioxy group is for example methylenedioxy and ethylenedioxy.

A branched or straight C$_1$–C$_6$ alkylene chain is, preferably, a branched or straight C$_1$–C$_4$ alkylene chain, in particular, for example,

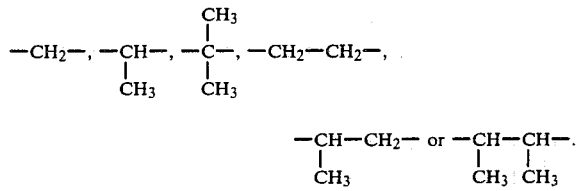

A branched or straight C$_2$–C$_6$ alkenylene chain is, preferably, a branched or straight C$_2$–C$_4$ alkenylene chain, in particular, for example,

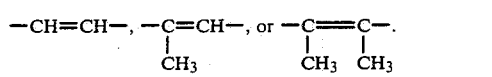

A C$_2$–C$_6$ alkanoyloxy group is, for example, acetoxy, propionyloxy and butyryloxy, preferably is acetoxy.

When one or more of R$_3$, R$_4$, R$_6$, R$_7$, R$_{11}$ and R$_{12}$ is a C$_1$–C$_6$ alkyl groups, the alkyl group is preferably a C$_1$–C$_4$ alkyl group, in particular methyl, ethyl, propyl and isopropyl. When one or more of R$_8$, R$_9$ and R$_{10}$ is a C$_1$–C$_6$ alkyl group, the alkyl group is preferably methyl, ethyl, propyl or butyl.

When one or more of R$_8$, R$_9$ and R$_{10}$ is a C$_1$–C$_6$ alkoxy group, the alkoxy group is preferably methoxy, ethoxy, propoxy, isopropoxy and butoxy.

When R$_6$ and R$_7$, taken together with the nitrogen atom to which they are linked, form an heterocyclic ring as defined above, it is preferably chosen from N-pirrolidinyl, N-piperazinyl unsubstituted or substituted by C$_1$–C$_3$ alkyl and morpholino unsubstituted or substituted by methyl.

Preferred compounds of the invention are the compounds of formula (I), wherein n is 1 or 2;

R$_1$ is carboxy or 2-[di-(C$_1$–C$_2$)alkylamino]-ethoxycarbonyl; 5-tetrazolyl; amino, hydroxy or C$_1$–C$_2$ alkoxy-carbonylamino; methyl; a group —NHR$_{13}$ or —OR$_{13}$, wherein R$_{13}$ is (a''') —COCOOH or —CO—CH=CH—COOH,(b''') —CO—A'—R$_{14}$, wherein A' is a phenylene group or a —(CH$_2$)-$_p$—moiety, wherein p is 1, 2 or 3 and R$_{14}$ is carboxy or a group

wherein R$_6$ and R$_7$ are as defined above, or R$_{13}$ is (c''') a group —(CH$_2$)$_q$—COOH wherein q is 1, 2 or 3;

R$_2$ is thienyl or pyridyl, wherein the thienyl and the pyridyl are unsubstituted or substituted by a C$_1$–C$_3$ alkyl group or R$_2$ is a group

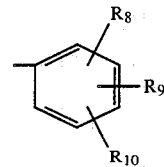

wherein each of R$_8$, R$_9$ and R$_{10}$ is independently hydrogen, fluorine, chlorine, C$_1$–C$_2$ alkyl, hydroxy, C$_1$–C$_3$ alkoxy, acetoxy, carboxy, amino, di-(C$_1$–C$_2$)alkylamino, or any two adjacent R$_8$, R$_9$ and R$_{10}$ groups, taken together form a methylenedioxy group; and the pharmaceutically acceptable salts thereof.

More preferred compounds of the invention are the compounds of formula (I), wherein n is 1 or 2;

R$_1$ is carboxy or 2-[di-(C$_1$–C$_2$)alkylamino]-ethoxycarbonyl; 5-tetrazolyl; amino, hydroxy or C$_1$–C$_2$ alkoxy-carbonylamino; methyl; a group —NHR$_{13}$ or —OR$_{13}$, wherein R$_{13}$ is (a''') —COCOOH or —CO—CH=CH—COOH, (b''') —CO—(CH$_2$-)$_p$—R$_{14}$, wherein p is 1 or 2 and R$_{14}$ is carboxy or a group

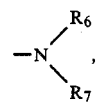

wherein each of R$_6$ and R$_7$ is independently hydrogen or C$_1$–C$_4$ alkyl or R$_6$ and R$_7$, taken together with the nitrogen atom to which they are linked, form a N-piperazinyl ring unsubstituted or substituted by C$_1$–C$_3$ alkyl, or a morpholino ring unsubstituted or substituted by methyl; or R$_{13}$ is (c''') a group —(CH$_2$)$_q$—COOH, wherein q is 1 or 2;

R$_2$ is thienyl or pyridyl, wherein the thienyl and the pyridyl are unsubstituted or substituted by a methyl group or R$_2$ is a group

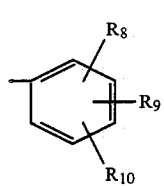

wherein each of R$_8$, R$_9$ and R$_{10}$ is independently hydrogen, fluorine, chlorine, C$_1$–C$_2$ alkyl, hydroxy, C$_1$–C$_3$ alkoxy, acetoxy, carboxy, amino, di-(C$_1$–C$_2$)alkylamino, or any two adjacent R$_8$, R$_9$ and R$_{10}$ groups, taken together form a methylenedioxy group; and the pharmaceutically acceptable salts thereof.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, tris-(hydroxymethyl)-aminomethane, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic, nitric and sulphuric acids and with organic acids, e.g. citric, tartaric maleic, malic, fumaric, methanesulphonic and ethanesulphonic acids.

Examples of particularly preferred compounds of the invention are:
4-benzylidene-1,2,3,4-tetrahydro-9-oxo-9H-xanthen-7-carboxylic acid;
4-(2-methyl-benzylidene)-1,2,3,4-tetrahydro-9-oxo-9H-xanthen-7-carboxylic acid;
3-benzylidene-1,2,3,9-tetrahydro-9-oxo-cyclopenta[b][1]benzopyran-7-carboxylic acid;
3-(2-methyl-benzylidene)-1,2,3,9-tetrahydro-9-oxo-cyclopenta[b][1]benzopyran-7-carboxylic acid;
3-(3-methoxy-benzylidene)-1,2,3,9-tetrahydro-9-oxo-cyclopenta[b][1]benzopyran-7-carboxylic acid;
3-(4-methoxy-benzylidene)-1,2,3,9-tetrahydro-9-oxo-cyclopenta[b][1]benzopyran-7-carboxylic acid;
3-(2,3-dimethoxy-benzylidene)-1,2,3,9-tetrahydro-9-oxo-cyclopenta[b][1]benzopyran-7-carboxylic acid;
3-(2,5-dimethoxy-benzylidene)-1,2,3,9-tetrahydro-9-oxo-cyclopenta[b][1]benzopyran-7-carboxylic acid;
3-(4-fluoro-benzylidene)-1,2,3,9-tetrahydro-9-oxo-cyclopenta[b][1]benzopyran-7-carboxylic acid;
3-(2-chloro-benzylidene)-1,2,3,9-tetrahydro-9-oxo-cyclopenta[b][1]benzopyran-7-carboxylic acid;
3-(3-chloro-benzylidene)-1,2,3,9-tetrahydro-9-oxo-cyclopenta[b][1]benzopyran-7-carboxylic acid;
3-(4-chloro-benzylidene)-1,2,3,9-tetrahydro-9-oxo-cyclopenta[b][1]benzopyran-7-carboxylic acid;
3-(2-ethoxy-benzylidene)-1,2,3,9-tetrahydro-9-oxo-cyclopenta[b][1]benzopyran-7-carboxylic acid;
3-benzylidene-6-N-(2-morpholino-ethyl)-amino-1,2,3,9-tetrahydro-cyclopenta[b][1]benzopyran-9-one;
3-(3-ethoxy-benzylidene)-1,2,3,9-tetrahydro-9-oxo-cyclopenta[b][1]benzopyran-7-carboxylic acid;
3-(4-ethoxy-benzylidene)-1,2,3,9-tetrahydro-9-oxo-cyclopenta[b][1]benzopyran-7-carboxylic acid;
3-(2,5-dimethyl-benzylidene)-1,2,3,9-tetrahydro-9-oxo-cyclopenta[b][1]benzopyran-7-carboxylic acid;
3-(2-methoxy-3-ethoxy-benzylidene)-1,2,3,9-tetrahydro-9-oxo-cyclopenta[b][1]benzopyran-7-carboxylic acid;
N-(3-benzylidene-1,2,3,9-tetrahydro-9-oxo-cyclopenta[b][1]benzopyran-6-yl)-amino-oxacetic acid;
N-[3-(2-methyl-benzylidene)-1,2,3,9-tetrahydro-9-oxo-cyclopenta[b][1]benzopyran-6-yl]-amino-oxacetic acid;
N-[3-(2-chloro-benzylidene)-1,2,3,9-tetrahydro-9-oxo-cyclopenta[b][1]benzopyran-6-yl]-amino-oxoacetic acid;
N-[3-(4-chloro-benzylidene)-1,2,3,9-tetrahydro-9-oxo-cyclopenta[b][1]benzopyran-6-yl]-amino-oxoacetic acid;
N-[3-(4-fluoro-benzylidene)-1,2,3,9-tetrahydro-9-oxo-cyclopenta[b][1]benzopyran-6-yl]-amino-oxoacetic acid;
N-[3-(4-ethoxy-benzylidene)-1,2,3,9-tetrahydro-9-oxo-cyclopenta[b][1]benzopyran-6-yl]-amino-oxoacetic acid;
N-[3-(4-methoxy-benzylidene)-1,2,3,9-tetrahydro-9-oxo-cyclopenta[b][1]benzopyran-6-yl]-amino-oxoacetic acid;
N-[3-(2,5-dimethyl-benzylidene)-1,2,3,9-tetrahydro-9-oxo-cyclopenta[b][1]benzopyran-6-yl]-amino-oxoacetic acid;
N-[3-(2,3-dimethoxy-benzylidene)-1,2,3,9-tetrahydro-9-oxo-cyclopenta[b][1]benzopyran-6-yl]-amino-oxoacetic acid;
N-[3-(2,6-dichloro-benzylidene)-1,2,3,9-tetrahydro-9-oxo-cyclopenta[b][1]benzopyran-6-yl]-amino-oxoacetic acid;
N-[3-(3-chloro-benzylidene)-1,2,3,9-tetrahydro-9-oxo-cyclopenta[b][1]benzopyran-6-yl]-amino-oxoacetic acid;
(3-benzylidene-1,2,3,9-tetrahydro-9-oxo-cyclopenta[b][1]benzopyran-6-yloxy)-acetic acid;
(E)-3-[N-(3-benzylidene-1,2,3,9-tetrahydro-9-oxo-cyclopenta[b][1]benzopyran-6-yl)-aminocarbonyl]-2-propenoic acid;
(Z)-3-[N-(3-benzylidene-1,2,3,9-tetrahydro-9-oxo-cyclopenta[b][1]benzopyran-6-yl)-aminocarbonyl]-2-propenoic acid;
and the pharmaceutically acceptable salts thereof, in particular the sodium, triethanolamine and tris-(hydroxy-methyl)-aminomethane salts and the hydrochlorides, and the basic esters (e.g. those with 2-diethylamino-ethanol) and the $C_1$-$C_6$ alkyl esters thereof, in particular the methyl, ethyl, isopropyl and n-butyl esters.

The compounds of formula (I) may be obtained by a process comprising
(a) reacting a compound of formula (II)

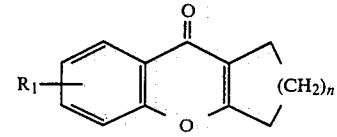

wherein n and $R_1$ are as defined above or a salt thereof, with an aldehyde of formula (III)

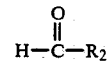

wherein $R_2$ is as defined above; or
(b) dehydrating a compound of formula (IV)

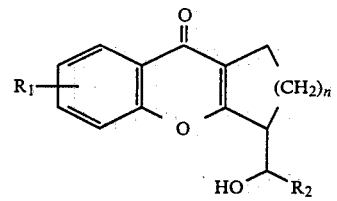

wherein n, $R_1$ and $R_2$ are as defined above; and if desired, converting a compound of formula (I) into another compound of formula (I) and/or, if desired, converting a compound of formula (I) into a pharmaceutically acceptable salt thereof and/or, if desired, converting a salt into a free compound and/or, if desired, separating a mixture of isomers into the single isomers.

Preferred salts of a compound of formula (II) are those with inorganic bases such as the sodium or potassium salts as well as the salts with inorganic acids e.g. hydrochloric, hydrobromic, hydroiodic and sulphuric acid. The reaction of a compound of formula (II) with an aldehyde of formula (III) may be carried out, for example, in the presence of basic condensing agents, for example, sodium ethoxide, sodium methoxide, potassium tert.butoxide, sodium hydride, sodium amide, in a solvent, preferably selected from the group consisting of methanol, ethanol, dioxane, dimethylformamide and their mixtures, at a temperature ranging between 0° C. and about 100° C.

During the reaction of a compound of formula (II) with a compound of formula (III) the intermediate compounds of formula (IV) are formed, which usually are not isolated because spontaneously dehydrate to give the corresponding compounds of formula (I): only in a few cases, depending on the nature of the aldehyde (III) and on the experimental conditions (e.g., reaction temperature ranging from 0° C. to about room temperature), the compounds of formula (IV) can be isolated and further processed to give the compounds of formula (I).

The dehydration of a compound of formula (IV) may be carried out, for example, by acid catalysis, by heating the compound in a solvent such as methanol, ethanol, dioxane or acetic acid in the presence of an acid such as HCl, HBr, HI, $H_2SO_4$, p-toluenesulphonic or methanesulphonic acid, at a temperature ranging from about 50° C. to the reflux temperature.

Alternatively the dehydration of a compound of formula (IV) may be carried out by basic catalysis by heating the compound in a solvent such as methanol, ethanol or dioxane, in the presence of a base such as NaOH, KOH, $K_2CO_3$, $Na_2CO_3$, $NaOCH_3$, $NaOC_2H_5$, at a temperature ranging from about 50° C. to the reflux temperature.

A compound of formula (I) may be converted, as stated above, into another compound of formula (I) by known methods; for example, a compound of formula (I) wherein $R_1$ is a $C_1$-$C_6$ alkoxycarbonyl group may be converted into a compound of formula (I), wherein $R_1$ is a free carboxy group, by hydrolysis, e.g. basic hydrolysis, using, for example, sodium or potassium hydroxide, in a solvent, such as water, dioxane, dimethylformamide or a lower aliphatic alcohol and their mixtures, and operating at a temperature ranging from the room temperature to about 100° C.; the same reaction may be also carried out e.g. by treatment with lithium bromide in dimethylformamide at a temperature higher than 50° C. or by treatment with hydrochloric or hydrobromic or hydroiodic or sulphuric acid in acetic acid at temperature higher than 50° C.

A compound of formula (I) wherein $R_1$ is a free carboxy group may be converted into a compound of formula (I) wherein $R_1$ is a $C_1$-$C_6$ alkoxycarbonyl group unsubstituted or substituted by a di-($C_1$-$C_6$)alkyl-amino group by converting the carboxylic acid into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of solvents or in an inert organic solvent such as benzene, toluene, xylene, dioxane, dichloroethane, methylene chloride or tetrahydrofuran, at a temperature ranging preferably from about 0° to about 120° C., and then reacting the resulting halocarbonyl derivative with a suitable $C_1$-$C_6$ alkyl alcohol, unsubstituted or substituted by a di-($C_1$-$C_6$)alkyl-amino group, in an inert solvent such as benzene, toluene, xylene, dioxane, dichloroethane, methylene chloride or tetrahydrofuran, at temperature varying between about 0° C. and about 120° C., preferably in the presence of a base such as triethylamine or pyridine.

Alternatively the esterification of a free carboxy group in a compound of formula (I) may be effected, for example, by reacting the acid with a suitable optionally substituted $C_1$-$C_6$ alkyl alcohol in the presence of a Lewis acid such as gaseous hydrochloric acid, 98% sulphuric acid, boron trifluoride etherate at a temperature varying from room temperature and the reflux temperature.

Furthermore, for example, a compound of formula (I) wherein $R_1$ is a free amino group may be converted into a compound of formula (I) wherein $R_1$ is a group —NH—CO—A—COOH, wherein A is as defined above, except a single bond, by reaction with a compound of formula

wherein A is as defined above, except a single bond, in an inert solvent such as dichloromethane, dichloroethane, chloroform, tetrahydrofuran, dimethylformamide, dimethylacetamide, at a temperature varying between room temperature and about 100° C.

Alternatively, for example, a compound of formula (I) wherein $R_1$ is a group of formula —NH—CO—A—COOH, wherein A is as defined above, may be obtained by reacting a compound of formula (I) wherein $R_1$ is a free amino group with a compound of formula ZCO—A—R'$_5$, wherein A is as defined above, Z is halogen, preferably chlorine, and R'$_5$ is a $C_1$-$C_6$ alkoxycarbonyl group, under the same experimental conditions as defined above for the reaction of a compound of formula (I) with a compound of formula (V), so to obtain a compound of formula (I) wherein $R_1$ is a group —NHCO—A—R'$_5$, wherein A and R'$_5$ are as defined above, which compound is in turn converted into a compound of formula (I) wherein $R_1$ is a group —NHCO—A—COOH, wherein A is as defined above, for example, by basic hydrolysis, using aqueous NaOH or KOH in a solvent such as dioxane, dimethylformamide, dimethylacetamide at a temperature varying from 0° C. to about 50° C.

Furthermore, a compound of formula (I) wherein $R_1$ is a group —NH—(CO)$_m$—A—R''$_5$, wherein m and A are as defined above and R''$_5$ is halomethyl may be converted into a compound of formula (I) wherein $R_1$ is a group

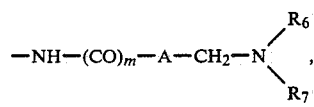

wherein m, A, $R_6$ and $R_7$ are as defined above, for example, by reaction with a compound of formula

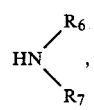

wherein $R_6$ and $R_7$ are as defined above, in an inert organic solvent such as dioxane, dimethylformamide, dimethylacetamide, at a temperature varying between the room temperature and the reflux temperature, preferably between the room temperature and about 100° C. Furthermore, for example, a compound of formula (I) wherein $R_1$ is a group

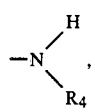

wherein $R_4$ is as defined above, may be converted into a compound of formula (I) wherein $R_1$ is a group

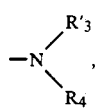

wherein $R_4$ is as defined above and $R'_3$ is $C_1-C_6$ alkyl, by reacting with a suitable $C_1-C_6$ alkyl halide in the presence of a base such as $Na_2CO_3$, $K_2CO_3$, NaH, $NaNH_2$, in a solvent such as dimethylformamide, dimethylacetamide, dioxane, tetrahydrofuran and their mixtures, at a temperature varying between room temperature and about 100° C.

Furthermore, for example, a compound of formula (I) wherein $R_1$ is a formylamino or a $C_2-C_6$ alkanoylamino group, may be converted into a compound of formula (I) wherein $R_1$ is a free amino group by acid hydrolysis using, for example, hydrochloric, hydrobromic or hydroiodic acid in aqueous solution in the presence, if necessary, of an organic cosolvent such as dioxane or acetic acid, operating at a temperature varying between room temperature and reflux temperature.

Furthermore, for example, a nitro group may be converted into an amino group by treatment, for example, with stannous chloride in concentrated hydrochloric acid, using, if necessary, an organic cosolvent such as acetic acid, dioxane, tetrahydrofuran, at a temperature ranging between room temperature and about 100° C.

Furthermore, for example, a free hydroxy or amino group, may be converted respectively into a $C_2-C_6$ alkanoyloxy or $C_2-C_6$ alkanoylamino group using conventional methods well known in organic chemistry.

Furthermore, for example, a compound of formula (I), wherein $R_1$ is carboxy, may be converted into a compound of formula (I), wherein $R_1$ is 5-tetrazolyl by known methods, for example, by converting the carboxy group into the corresponding halide, preferably the chloride, by reaction, e.g., with thionyl chloride in benzene or dioxane or dichloroethane, at a temperature ranging from the room temperature to about 100° C., then by reacting the halide with ammonia, at room temperature in one of the above mentioned solvents, to give the corresponding amide and by dehydrating the amide to give the nitrile, e.g., by means of p-toluenesulphonyl chloride in pyridine and dimethylformamide, at a temperature ranging from about 30° C. to about 100° C., and finally reacting the nitrile with sodium azide and ammonium chloride in dimethylformamide at a temperature ranging from the room temperature to about 100° C.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active base or with an optically active acid and subsequent fractional crystallization.

Thus, the separation of a mixture of geometric isomers may be carried out, for example, by fractional crystallization.

The compounds of formula (II) may be prepared, for example by reacting a compound of formula (VI)

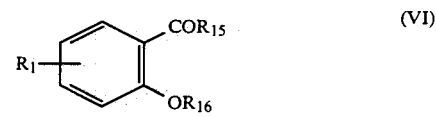

wherein $R_1$ is as defined above, $R_{15}$ is halogen, preferably chlorine and bromine, or a group $-OCOOR_{17}$, wherein $R_{17}$ is $C_1-C_6$ alkyl, phenyl or benzyl, and $R_{16}$ is a $C_1-C_{10}$ acyl radical, preferably a $C_1-C_6$ alkanoyl radical, in particular acetyl, with a compound of formula (VII)

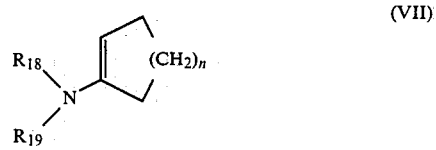

wherein n is as defined above and each of $R_{18}$ and $R_{19}$ is independently $C_1-C_6$ alkyl or $R_{18}$ and $R_{19}$, taken together with the nitrogen atom to which then are linked, form a N-pyrrolidinyl, a morpholino or a piperidino radical, wherein the piperidino ring is unsubstituted or substituted by one or two methyl groups.

The reaction between a compound of formula (VI) and a compound of formula (VII) may be carried out, for example, in an inert solvent such as benzene, toluene, chloroform, dichloromethane, dichloroethane, dioxane, at a temperature varying between about 0° C. and about 50° C. so as to obtain an intermediate compound, having presumably the formula (VIII)

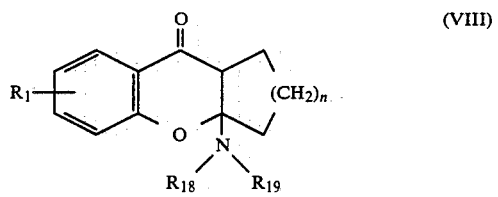

wherein n, $R_1$, $R_{18}$ and $R_{19}$ are as defined above; the compound of formula (VIII), which is not usually isolated from the reaction mixture, is in turn converted into a compound of formula (II), e.g. by heating with aqueous organic basis, such as pyridine or piperidine.

The compounds of formula (III), (VI) and (VII) are known compounds or may be prepared by conventional methods: in some cases they are commercially available products. The compounds of the invention are useful for the prevention and the treatment of all the diseases in which anaphylactic mediators are involved, for example, the allergic affections.

Therefore the compounds of the invention are useful in the prevention and treatment, e.g., of allergic rhinitis, hay fever, urticaria, dermatitis and, in particular they are effective in the prevention and treatment of the allergic bronchial asthma.

The activity of the compounds of the invention is shown, e.g., by the fact that they are active in the following biological tests:

in vitro
(1) test of A 23187 induced SRS production from rat peritoneal cells, according to M. K. Bach and J. R. Brashler (J. Immunol., 113, 2040, 1974);
(2) test of antigen induced SRS production from guinea-pig chopped lung, according to W. E. Brochlehurst (J. Physiol., 151, 416, 1960);

in vivo
(3) test of the IgE mediated passive cutaneous anaphylaxis (PCA) in the rat, according to A. M. J. N. Blair (Immunology, 16, 749, 1969).

The results of these biological tests show that the compounds of the invention are active, for example, as inhibitors of the immunological release of mediators, e.g. histamine, from the mast cells and as inhibitors of the production and/or release of anaphylactic mediators such as "slow reacting substances" (SRS) in the peritoneal and the pulmonary system, induced by challenge with an ionophore or with an antigen.

As preferred example of compound having antiallergic activity the following can be mentioned:
3-(2-methyl-benzylidene)-1,2,3,9-tetrahydro-9-oxo-cyclopenta[b][1]benzopyran-7-carboxylic acid.

In view of their high therapeutic index the compounds of the invention can be safely used in medicine. For example, the approximate acute toxicity ($LD_{50}$) of the compound 3-(2-methyl-benzylidene)-1,2,3,9-tetrahydro-9-oxo-cyclopenta[b][1]benzopyran-7-carboxylic acid in the mouse, determined with single administration of increasing doses and measured on the seventh day after the day of treatment is per os higher than 800 mg/kg. Analogous toxicity data have been found for the other compounds of the invention.

The compounds of the invention may be administered in conventional manner, for instance, orally or parenterally at a daily dosage preferably from about 0.5 to about 15 mg/kg, or by inhalation, preferably at a daily dosage from about 0.5 to about 100 mg, preferably 0.5 to 25 mg, or by topical application, (for example for the treatment of urticaria and dermatosis), e.g. by a cream containing about from 0.5 to 5 mg, preferably 1-2 mg, of the active principle per 100 mg of cream.

The nature of the pharmaceutical compositions containing the compounds of this invention in association with pharmaceutically acceptable carriers or diluents will, of course, depend upon the desired route of administration. The compositions may be formulated in the conventional ways with the usual ingredients. For example, the compounds of the invention may be administered in the form of aqueous or oily solutions or suspensions, aerosols, as well as powders, tablets, pills, gelatine capsules, syrups, drops, suppositories, or creams, or lotions for topical use.

Thus, for oral administration, the pharmaceutical compositions containing the compouns of this invention, are preferably tablets, pills or gelatine capsules which contain the active substance together with diluents, such as lactose, dextrose, sucrose, mannitol, sorbitol, cellulose; lubricants, for instance, silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents such as lecithin, polisorbates, laurylsulphates; and, in general, non-toxic and pharmacologically inactive substances used in pharmaceutical formulations.

Said pharmaceutical preparations may be manufactured in known manner, for example, by means of mixing, granulating, tabletting, sugar-coating, or film-coating processes. For the treatment of allergic asthma, the compounds of the invention are also administered by inhalation. For such use, suitable compositions may comprise a suspension or solution of the active ingredient, preferably in the form of a salt, such as the sodium salt or the salt with triethanolamine or with tris-(hydroxymethyl)-aminomethane, in water, for administration by means of a conventional nebulizer.

Alternatively, the compositions may comprise a suspension or a solution of the active ingredient in a conventional liquified propellant, such as dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or surface-active agent to the composition, in order to suspend the medicament in the propellant medium and such surface-active agents may be any of those commonly used for this purpose, such as non-ionic surface-active agents, e.g., lecithin.

The compounds of the invention may also be administered in the form of powders by means of a suitable insufflator device and in this case the fine particle sized powders of the active ingredients may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g. as creams lotions or pastes for use in dermatological treatments.

For these compositions the active ingredient may be mixed with conventional oleaginous or emulsifying excipients. The following examples illustrate but do not limit the present invention.

EXAMPLE 1

1,2,3,9-tetrahydro-9-oxo-cyclopenta[b][1]benzopyran-7-carboxylic acid, methyl ester, m.p. 156°–158° C. (5.1 g) was reacted with 2-methyl benzaldehyde (3.3 g) in methanol (80 ml) in the presence of sodium methylate (2.28 g) under stirring at room temperature for 20 hours. The precipitate was filtered and washed with methanol and then with water until neutral: crystallization from $CH_2Cl_2$-methanol gave 5.2 g of 3-(2-methyl-benzylidene)-1,2,3,9-tetrahydro-9-oxo-cyclopenta[b][1]benzopyran-7-carboxylic acid, methyl ester, m.p. 203°–205° C.

By proceeding analogously the following compounds were prepared:
3-benzylidene-1,2,3,9-tetrahydro-9-oxo-cyclopenta[b][1]benzopyran-7-carboxylic acid, methyl ester, m.p. 216°–218° C.;
3-(3-methyl-benzylidene)-1,2,3,9-tetrahydro-9-oxo-cyclopenta[b][1]benzopyran-7-carboxylic acid, methyl ester, m.p. 202°–204° C.;

3-(4-methyl-benzylidene)-1,2,3,9-tetrahydro-9-oxo-cyclopenta[b][1]benzopyran-7-carboxylic acid, methyl ester, m.p. 205°-207° C.;

3-(2-methoxy-benzylidene)-1,2,3,9-tetrahydro-9-oxo-cyclopenta[b][1]benzopyran-7-carboxylic acid, methyl ester, m.p. 209°-211° C.;

3-(3-methoxy-benzylidene)-1,2,3,9-tetrahydro-9-oxo-cyclopenta[b][1]benzopyran-7-carboxylic acid, methyl ester, m.p. 181°-183° C.;

3-(4-methoxy-benzylidene)-1,2,3,9-tetrahydro-9-oxo-cyclopenta[b][1]benzopyran-7-carboxylic acid, methyl ester, m.p. 204°-207° C.;

3-(2,3-dimethoxy-benzylidene)-1,2,3,9-tetrahydro-9-oxo-cyclopenta[b][1]benzopyran-7-carboxylic acid, methyl ester, m.p. 251°-253° C.;

3-(2,5-dimethoxy-benzylidene)-1,2,3,9-tetrahydro-9-oxo-cyclopenta[b][1]benzopyran-7-carboxylic acid, methyl ester, m.p. 193°-195° C.;

3-(4-fluoro-benzylidene)-1,2,3,9-tetrahydro-9-oxo-cyclopenta[b][1]benzopyran-7-carboxylic acid, methyl ester, m.p. 219°-222° C.;

3-(2-chloro-benzylidene)-1,2,3,9-tetrahydro-9-oxo-cyclopenta[b][1]benzopyran-7-carboxylic acid, methyl ester;

3-(3-chloro-benzylidene)-1,2,3,9-tetrahydro-9-oxo-cyclopenta[b][1]benzopyran-7-carboxylic acid, methyl ester, m.p. 217°-220° C.;

3-(4-chloro-benzylidene)-1,2,3,9-tetrahydro-9-oxo-cyclopenta[b][1]benzopyran-7-carboxylic acid, methyl ester, m.p. 208°-211° C.;

3-(2-ethoxy-benzylidene)-1,2,3,9-tetrahydro-9-oxo-cyclopenta[b][1]benzopyran-7-carboxylic acid, methyl ester;

3-(3-ethoxy-benzylidene)-1,2,3,9-tetrahydro-9-oxo-cyclopenta[b][1]benzopyran-7-carboxylic acid, methyl ester, m.p. 189°-192° C.;

3-(2,4-dimethyl-benzylidene)-1,2,3,9-tetrahydro-9-oxo-cyclopenta[b][1]benzopyran-7-carboxylic acid, methyl ester;

3-(4-ethoxy-benzylidene)-1,2,3,9-tetrahydro-9-oxo-cyclopenta[b][1]benzopyran-7-carboxylic acid, methyl ester, m.p. 212°-214° C.;

3-(2,4-dimethoxy-benzylidene)-1,2,3,9-tetrahydro-9-oxo-cyclopenta[b][1]benzopyran-7-carboxylic acid, methyl ester;

3-(3,5-dimethoxy-benzylidene)-1,2,3,9-tetrahydro-9-oxo-cyclopenta[b][1]benzopyran-7-carboxylic acid, methyl ester;

3-(3,4-dimethoxy-benzylidene)-1,2,3,9-tetrahydro-9-oxo-cyclopenta[b][1]benzopyran-7-carboxylic acid, methyl ester, m.p. 260°-264° C.;

3-(2,5-dimethyl-benzylidene)-1,2,3,9-tetrahydro-9-oxo-cyclopenta[b][1]benzopyran-7-carboxylic acid, methyl ester, m.p. 210°-213° C.;

3-(3,4-methylenedioxy-benzylidene)-1,2,3,9-tetrahydro-9-oxo-cyclopenta[b][1]benzopyran-7-carboxylic acid, methyl ester, m.p. 270°-272° C.;

3-(2-methoxy-3-ethoxy-benzylidene)-1,2,3,9-tetrahydro-9-oxo-cyclopenta[b][1]benzopyran-7-carboxylic acid, methyl ester;

3-(2-ethoxy-3-methoxy-benzylidene)-1,2,3,9-tetrahydro-9-oxo-cyclopenta[b][1]benzopyran-7-carboxylic acid, methyl ester;

3-(2,3,4-trimethoxy-benzylidene)-1,2,3,9-tetrahydro-9-oxo-cyclopenta[b][1]benzopyran-7-carboxylic acid, methyl ester;

3-(2,4,5-trimethoxy-benzylidene)-1,2,3,9-tetrahydro-9-oxo-cyclopenta[b][1]benzopyran-7-carboxylic acid, methyl ester;

3-(3,4,5-trimethoxy-benzylidene)-1,2,3,9-tetrahydro-9-oxo-cyclopenta[b][1]benzopyran-7-carboxylic acid, methyl ester, m.p. 221°-224° C.;

3-(4-N,N-dimethylamino-benzylidene)-1,2,3,9-tetrahydro-9-oxo-cyclopenta[b][1]benzopyran-7-carboxylic acid, methyl ester, m.p. 224°-226° C.;

3-(4-hydroxy-benzylidene)-1,2,3,9-tetrahydro-9-oxo-cyclopenta[b][1]benzopyran-7-carboxylic acid, methyl ester;

3-(4-nitro-benzylidene)-1,2,3,9-tetrahydro-9-oxo-cyclopenta[b][1]benzopyran-7-carboxylic acid, methyl ester;

3-(2-propoxy-benzylidene)-1,2,3,9-tetrahydro-9-oxo-cyclopenta[b][1]benzopyran-7-carboxylic acid, methyl ester;

3-(3-propoxy-benzylidene)-1,2,3,9-tetrahydro-9-oxo-cyclopenta[b][1]benzopyran-7-carboxylic acid, methyl ester;

3-(4-propoxy-benzylidene)-1,2,3,9-tetrahydro-9-oxo-cyclopenta[b][1]benzopyran-7-carboxylic acid, methyl ester;

3-(2-isopropoxy-benzylidene)-1,2,3,9-tetrahydro-9-oxo-cyclopenta[b][1]benzopyran-7-carboxylic acid, methyl ester;

3-(3-isopropoxy-benzylidene)-1,2,3,9-tetrahydro-9-oxo-cyclopenta[b][1]benzopyran-7-carboxylic acid, methyl ester;

3-(4-isopropoxy-benzylidene)-1,2,3,9-tetrahydro-9-oxo-cyclopenta[b][1]benzopyran-7-carboxylic acid, methyl ester;

3-(2,6-dichloro-benzylidene)-1,2,3,9-tetrahydro-9-oxo-cyclopenta[b][1]benzopyran-7-carboxylic acid, methyl ester, m.p. 168°-170° C.;

3-(3,4-dichloro-benzylidene)-1,2,3,9-tetrahydro-9-oxo-cyclopenta[b][1]benzopyran-7-carboxylic acid, methyl ester, m.p. 237°-240° C.;

3-(2,4-dichloro-benzylidene)-1,2,3,9-tetrahydro-9-oxo-cyclopenta[b][1]benzopyran-7-carboxylic acid, methyl ester, m.p. 255°-258° C.;

3-(2-fluoro-benzylidene)-1,2,3,9-tetrahydro-9-oxo-cyclopenta[b][1]benzopyran-7-carboxylic acid, methyl ester; and 3-(3-fluoro-benzylidene)-1,2,3,9-tetrahydro-9-oxo-cyclopenta[b][1]benzopyran-7-carboxylic acid, methyl ester.

EXAMPLE 2

3-(2-methyl-benzylidene)-1,2,3,9-tetrahydro-9-oxo-cyclopenta[b][1]benzopyran-7-carboxylic acid, methyl ester (3 g) was hydrolized by treatment with 1% KOH in 95% ethanol (59 ml) at reflux temperature for 15 minutes. After cooling, acidification with HCl and dilution with ice water, the precipitate was filtered and washed with water. Crystallization from dimethylformamide-ethanol gave 2.4 g of 3-(2-methyl-benzylidene)-1,2,3,9-tetrahydro-9-oxo-cyclopenta[b][1]benzopyran-7-carboxylic acid, m.p. 296°-298° C., NMR (CF$_3$COOD) δppm: 2.59 (s) (3H, —CH$_3$), 3.40 (bs) (4H, C-1 and C-2 protons), 7.38-7.87 (m) (4H, phenyl protons), 8.10 (d) (1H, C-5 proton), 8.30 (bs) (1H, =CH—), 8.80 (dd) (1H, C-6 proton), 9.30 (d) (1H, C-8 proton).

By proceeding analogously the following compounds were prepared:

3-benzylidene-1,2,3,9-tetrahydro-9-oxo-cyclopenta[b][1]benzopyran-7-carboxylic acid, m.p. 344°-347° C.;

3-(3-methyl-benzylidene-1,2,3,9-tetrahydro-9-oxo-cyclopenta[b][1]benzopyran-7-carboxylic acid, m.p. 309°-310° C.;

3-(4-methyl-benzylidene)-1,2,3,9-tetrahydro-9-oxo-cyclopenta[b][1]benzopyran-7-carboxylic acid, m.p. 340°-342° C.;

3-(2-methoxy-benzylidene)-1,2,3,9-tetrahydro-9-oxo-cyclopenta[b][1]benzopyran-7-carboxylic acid, m.p. 291°-295° C.;

3-(3-methoxy-benzylidene)-1,2,3,9-tetrahydro-9-oxo-cyclopenta[b][1]benzopyran-7-carboxylic acid, m.p. 288°-290° C.;

3-(4-methoxy-benzylidene)-1,2,3,9-tetrahydro-9-oxo-cyclopenta[b][1]benzopyran-7-carboxylic acid, m.p. 320°-321° C.;

3-(2,3-dimethoxy-benzylidene)-1,2,3,9-tetrahydro-9-oxo-cyclopenta[b][1]benzopyran-7-carboxylic acid, m.p. 313°-314° C.;

3-(2,5-dimethoxy-benzylidene)-1,2,3,9-tetrahydro-9-oxo-cyclopenta[b][1]benzopyran-7-carboxylic acid, m.p. 320°-322° C.;

3-(4-fluoro-benzylidene)-1,2,3,9-tetrahydro-9-oxo-cyclopenta[b][1]benzopyran-7-carboxylic acid, m.p. 362°-363° C.;

3-(4-chloro-benzylidene)-1,2,3,9-tetrahydro-9-oxo-cyclopenta[b][1]benzopyran-7-carboxylic acid, m.p. 263°-264° C.;

3-(3-chloro-benzylidene)-1,2,3,9-tetrahydro-9-oxo-cyclopenta[b][1]benzopyran-7-carboxylic acid, m.p. 349°-350° C.;

3-(2-chloro-benzylidene)-1,2,3,9-tetrahydro-9-oxo-cyclopenta[b][1]benzopyran-7-carboxylic acid, m.p. 321°-324° C.;

3-(2-ethoxy-benzylidene)-1,2,3,9-tetrahydro-9-oxo-cyclopenta[b][1]benzopyran-7-carboxylic acid, m.p. 300°-302° C.;

3-(3-ethoxy-benzylidene)-1,2,3,9-tetrahydro-9-oxo-cyclopenta[b][1]benzopyran-7-carboxylic acid, m.p. 297°-299° C.;

3-(2,4-dimethyl-benzylidene)-1,2,3,9-tetrahydro-9-oxo-cyclopenta[b][1]benzopyran-7-carboxylic acid;

3-(4-ethoxy-benzylidene)-1,2,3,9-tetrahydro-9-oxo-cyclopenta[b][1]benzopyran-7-carboxylic acid, m.p. 329°-331° C.;

3-(2,4-dimethoxy-benzylidene)-1,2,3,9-tetrahydro-9-oxo-cyclopenta[b][1]benzopyran-7-carboxylic acid;

3-(3,5-dimethoxy-benzylidene)-1,2,3,9-tetrahydro-9-oxo-cyclopenta[b][1]benzopyran-7-carboxylic acid;

3-(3,4-dimethoxy-benzylidene)-1,2,3,9-tetrahydro-9-oxo-cyclopenta[b][1]benzopyran-7-carboxylic acid, m.p. 318°-319° C.;

3-(2,5-dimethyl-benzylidene)-1,2,3,9-tetrahydro-9-oxo-cyclopenta[b][1]benzopyran-7-carboxylic acid, m.p. 336°-337° C.;

3-(3,4-methylenedioxy-benzylidene)-1,2,3,9-tetrahydro-9-oxo-cyclopenta[b][1]benzopyran-7-carboxylic acid, m.p. 343°-345° C.;

3-(2-methoxy-3-ethoxy-benzylidene)-1,2,3,9-tetrahydro-9-oxo-cyclopenta[b][1]benzopyran-7-carboxylic acid, m.p. 308°-310° C.;

3-(2-ethoxy-3-methoxy-benzylidene)-1,2,3,9-tetrahydro-9-oxo-cyclopenta[b][1]benzopyran-7-carboxylic acid;

3-(2,3,4-trimethoxy-benzylidene)-1,2,3,9-tetrahydro-9-oxo-cyclopenta[b][1]benzopyran-7-carboxylic acid;

3-(2,4,5-trimethoxy-benzylidene)-1,2,3,9-tetrahydro-9-oxo-cyclopenta[b][1]benzopyran-7-carboxylic acid;

3-(3,4,5-trimethoxy-benzylidene)-1,2,3,9-tetrahydro-9-oxo-cyclopenta[b][1]benzopyran-7-carboxylic acid, m.p. 311°-313° C.;

3-(4-N,N-dimethylamino-benzylidene)-1,2,3,9-tetrahydro-9-oxo-cyclopenta[b][1]benzopyran-7-carboxylic acid, m.p. 350°-353° C.;

3-(2-fluoro-benzylidene)-1,2,3,9-tetrahydro-9-oxo-cyclopenta[b][1]benzopyran-7-carboxylic acid;

3-(3-fluoro-benzylidene)-1,2,3,9-tetrahydro-9-oxo-cyclopenta[b][1]benzopyran-7-carboxylic acid;

3-(4-hydroxy-benzylidene)-1,2,3,9-tetrahydro-9-oxo-cyclopenta[b][1]benzopyran-7-carboxylic acid;

3-(4-nitro-benzylidene)-1,2,3,9-tetrahydro-9-oxo-cyclopenta[b][1]benzopyran-7-carboxylic acid;

3-(2-propoxy-benzylidene)-1,2,3,9-tetrahydro-9-oxo-cyclopenta[b][1]benzopyran-7-carboxylic acid;

3-(3-propoxy-benzylidene)-1,2,3-9-tetrahydro-9-oxo-cyclopenta[b][1]benzopyran-7-carboxylic acid;

3-(4-propoxy-benzylidene)-1,2,3,9-tetrahydro-9-oxo-cyclopenta[b][1]benzopyran-7-carboxylic acid;

3-(2-isopropoxy-benzylidene)-1,2,3,9-tetrahydro-9-oxo-cyclopenta[b][1]benzopyran-7-carboxylic acid;

3-(3-isopropoxy-benzylidene)-1,2,3,9-tetrahydro-9-oxo-cyclopenta[b][1]benzopyran-7-carboxylic acid;

3-(4-isopropoxy-benzylidene)-1,2,3,9-tetrahydro-9-oxo-cyclopenta[b][1]benzopyran-7-carboxylic acid;

3-(2,6-dichloro-benzylidene)-1,2,3,9-tetrahydro-9-oxo-cyclopenta[b][1]benzopyran-7-carboxylic acid, m.p. 290°-292° C.;

3-(3,4-dichloro-benzylidene)-1,2,3,9-tetrahydro-9-oxo-cyclopenta[b][1]benzopyran-7-carboxylic acid, m.p. 353°-356° C.; and 3-(2,4-dichloro-benzylidene)-1,2,3,9-tetrahydro-9-oxo-cyclopenta[b][1]benzopyran-7-carboxylic acid, m.p. 340°-343° C.

EXAMPLE 3

1,2,3,9-tetrahydro-9-oxo-cyclopenta[b][1]benzopyran-7-carboxylic acid, methyl ester (3 g) was reacted with 6-methyl-2-pyridinecarboxaldehyde (1.95 g) in methanol (60 ml) in the presence of sodium methylate (1.35 g) under stirring at room temperature for 8 hours. The precipitate was filtered and washed with methanol and then with water until neutral. Purification over SiO$_2$ column using chloroform as eluent allowed to separate two components of the crude product of the reaction, both of which were crystallized from chloroform-isopropyl ether: 0.7 g of 3-[(6-methyl-2-pyridyl)-methylene]-1,2,3,9-tetrahydro-9-oxo-cyclopenta[b][1]benzopyran-7-carboxylic acid, methyl ester, m.p. 200°-202° C. and 1,4 g of 3-(α-hydroxy-6-methyl-2-picolyl)-1,2,3,9-tetrahydro-9-oxo-cyclopenta[b][1]benzopyran-7-carboxylic acid, methyl ester, m.p. 210°-212° C.

EXAMPLE 4

3-(α-hydroxy-6-methyl-2-picolyl)-1,2,3,9-tetrahydro-9-oxo-cyclopenta[b][1]benzopyran-7-carboxylic acid, methyl ester (1 g) was heated at the reflux temperature for 24 hours in methanol (30 ml) containing 37% HCl (1.5 ml).

After cooling, neutralization with NaOH and dilution with ice water, the precipitate was filtered and crystallized from methanol to give 0.6 g of 3-[(6-methyl-2-pyridyl)-methylene]-1,2,3,9-tetrahydro-9-oxo-cyclopenta[b][1]benzopyran-7-carboxylic acid, methyl ester, m.p. 200°-202° C., which was hydrolyzed by treatment with 0.5% KOH in 95% ethanol (23 ml) at the reflux temperature for 10 minutes. After cooling, neutralization with HCl and dilution with ice water, the precipitate was filtered and crystallized from methanol to give 0.4 g of 3-[(6-methyl-2-pyridyl)-methylene]-1,2,3,9-tetrahydro-9-oxo-cyclopenta[b][1]benzopyran-7-carboxylic acid, m.p. 250° C. dec., NMR (CDCl$_3$-CF$_3$COOD) δppm: 2.91 (s) (3H, —CH$_3$), 3.29 (bs) (4H, C-1 and C-2 protons), 7.52 (bs) (1H, =CH—), 7.75 (d) and 7.84 (d) and 8.04 (d) (3H, C-5 proton; C-3 and C-5 pyridyl protons), 8.50 (t) (1H, C-4 pyridyl proton), 8.63 (dd) (1H, C-6 proton), 9.12 (d) (1H, C-8 proton).

EXAMPLE 5

1,2,3,9-tetrahydro-9-oxo-cyclopenta[b][1]benzopyran-7-carboxylic acid, methyl ester (2 g), was reacted with 2-ethoxy-benzaldehyde (1.7 g) in methanol (55 ml) in the presence of sodium methylate (0.9 g) under stirring at room temperature for 24 hours. The precipitate, was filtered and washed with methanol and then with water until neutral: it was found to be a mixture of the compounds 3-(2-ethoxy-benzylidene)-1,2,3,9-tetrahydro-9-oxo-cyclopenta[b][1]benzopyran-7-carboxylic acid, methyl ester and 3-(α-hydroxy-2-ethoxy-benzyl)-1,2,3,9-tetrahydro-9-oxo-cyclopenta[b][1]benzopyran-7-carboxylic acid, methyl ester, m.p. 162°-168° C.

The mixture (1.7 g), without separation of the components, was heated with 37% HCl (17 ml) in acetic acid (17 ml) at the reflux temperature for 5 hours. After cooling the precipitate was filtered, washed with water and then crystallized from dioxane to give 1.2 g of 3-(2-ethoxy-benzylidene)-1,2,3,9-tetrahydro-9-oxo-cyclopenta[b][1]benzopyran-7-carboxylic acid, m.p. 300°-302° C., NMR (CDCl$_3$-CF$_3$COOD) δppm: 1.51 (t) (3H, —OCH$_2$CH$_3$), 3.17 (bs) (4H, C-1 and C-2 protons), 4.20 (q) (2H, —OCH$_2$CH$_3$), 7.04 (m) (2H, C-3 and C-5 phenyl protons), 7.41 (bt) (1H, C-4 phenyl proton), 7.60 (bd) (1H, C-6 phenyl proton), 7.85 (d) (1H, C-5 proton), 8.00 (bs) (1H, =CH—), 8.50 (dd) (1H, C-6 proton), 9.03 (d) (1H, C-8 proton).

EXAMPLE 6

1,2,3,9-tetrahydro-9-oxo-cyclopenta[b][1]benzopyran-7-carboxylic acid, m.p. 273°-275° C. (1.6 g) was reacted with 2-methoxy-benzaldehyde (1 g) in methanol (60 ml) in the presence of sodium methylate (1.3 g) under stirring at 45° C. for 7 hours. After cooling, the reaction mixture was acidified with 37% HCl and the precipitate was filtered and washed with methanol and then with water until neutral. Crystallization from chloroform-ethanol gave 1.2 g of 3-(2-methoxy-benzylidene)-1,2,3,9-tetrahydro-9-oxo-cyclopenta[b][1]benzopyran-7-carboxylic acid, m.p. 291°-295° C., NMR (CH$_3$COOD) δppm: 3.36 (bs) (4H, C-1 and C-2 protons), 4.09 (s) (3H, —OCH$_3$), 7.09-7.87 (m) (4H, phenyl protons), 8.07 (d) (1H, C-5 proton), 8.41 (bs) (1H, =CH—), 8.76 (dd) (1H, C-6 proton), 9.28 (d) (1H, C-8 proton).

EXAMPLE 7

By proceeding according to Examples 1, 2, 5 and 6 using suitable heterocyclic aldehydes, the following compounds were obtained:

3-(2-thenylidene)-1,2,3,9-tetrahydro-9-oxo-cyclopenta[b][1]benzopyran-7-carboxylic acid, methyl ester, m.p. 219°-222° C.;

3-(3-methyl-2-thenylidene)-1,2,3,9-tetrahydro-9-oxo-cyclopenta[b][1]benzopyran-7-carboxylic acid, methyl ester;

3-(5-methyl-2-thenylidene)-1,2,3,9-tetrahydro-9-oxo-cyclopenta[b][1]benzopyran-7-carboxylic acid, methyl ester;

3-[(2-pyridyl)-methylene]-1,2,3,9-tetrahydro-9-oxo-cyclopenta[b][1]benzopyran-7-carboxylic acid, methyl ester;

3-[(3-pyridyl)-methylene]-1,2,3,9-tetrahydro-9-oxo-cyclopenta[b][1]benzopyran-7-carboxylic acid, methyl ester, m.p. 250°-252° C.;

3-[(4-pyridyl)-methylene]-1,2,3,9-tetrahydro-9-oxo-cyclopenta[b][1]benzopyran-7-carboxylic acid, methyl ester;

3-(2-furfurylidene)-1,2,3,9-tetrahydro-9-oxo-cyclopenta[b][1]benzopyran-7-carboxylic acid, methyl ester, m.p. 203°-205° C.;

3-(5-methyl-2-furfurylidene)-1,2,3,9-tetrahydro-9-oxo-cyclopenta[b][1]benzopyran-7-carboxylic acid, methyl ester;

3-(2-thenylidene)-1,2,3,9-tetrahydro-9-oxo-cyclopenta[b][1]benzopyran-7-carboxylic acid, m.p. 344°-346° C.;

3-(3-methyl-2-thenylidene)-1,2,3,9-tetrahydro-9-oxo-cyclopenta[b][1]benzopyran-7-carboxylic acid;

3-(5-methyl-2-thenylidene)-1,2,3,9-tetrahydro-9-oxo-cyclopenta[b][1]benzopyran-7-carboxylic acid;

3-[(2-pyridyl)-methylene]-1,2,3,9-tetrahydro-9-oxo-cyclopenta[b][1]benzopyran-7-carboxylic acid;

3-[(3-pyridyl)-methylene]-1,2,3,9-tetrahydro-9-oxo-cyclopenta[b][1]benzopyran-7-carboxylic acid, m.p. 325°-328° C.;

3-[(4-pyridyl)-methylene]-1,2,3,9-tetrahydro-9-oxo-cyclopenta[b][1]benzopyran-7-carboxylic acid;

3-(2-furfurylidene)-1,2,3,9-tetrahydro-9-oxo-cyclopenta[b][1]benzopyran-7-carboxylic acid, m.p. 338°-343° C.; and 3-(5-methyl-2-furfurylidene)-1,2,3,9-tetrahydro-9-oxo-cyclopenta[b][1]benzopyran-7-carboxylic acid.

EXAMPLE 8

1,2,3,4-tetrahydro-9-oxo-9H-xanthen-7-carboxylic acid, methyl ester, m.p. 140°-142° C. (2 g), was reacted with benzaldehyde (1.1 g) in methanol (40 ml) in the presence of sodium methylate (0.75 g) under stirring at 50° C. for 24 hours.

After cooling the precipitate was filtered and washed with methanol and then with water: crystallization from CH$_2$Cl$_2$-methanol gave 1.3 g of 4-benzylidene-1,2,3,4-tetrahydro-9-oxo-9H-xanthen-7-carboxylic acid, methyl ester, m.p. 168°-170° C.

By proceeding analogously the following compounds were prepared:

4-(2-methyl-benzylidene)-1,2,3,4-tetrahydro-9-oxo-9H-xanthen-7-carboxylic acid, methyl ester;

4-(3-methyl-benzylidene)-1,2,3,4-tetrahydro-9-oxo-9H-xanthen-7-carboxylic acid, methyl ester;

4-(4-methyl-benzylidene)-1,2,3,4-tetrahydro-9-oxo-9H-xanthan-7-carboxylic acid, methyl ester;

4-(2-methoxy-benzylidene)-1,2,3,4-tetrahydro-9-oxo-9H-xanthen-7-carboxylic acid, methyl ester;

4-(3-methoxy-benzylidene)-1,2,3,4-tetrahydro-9-oxo-9H-xanthen-7-carboxylic acid, methyl ester;

4-(4-methoxy-benzylidene)-1,2,3,4-tetrahydro-9-oxo-9H-xanthen-7-carboxylic acid, methyl ester;

4-(2-ethoxy-benzylidene)-1,2,3,4-tetrahydro-9-oxo-9H-xanthen-7-carboxylic acid, methyl ester;

4-(3-ethoxy-benzylidene)-1,2,3,4-tetrahydro-9-oxo-9H-xanthen-7-carboxylic acid, methyl ester;
4-(4-ethoxy-benzylidene)-1,2,3,4-tetrahydro-9-oxo-9H-xanthen-7-carboxylic acid, methyl ester;
4-(2,5-dimethyl-benzylidene)-1,2,3,4-tetrahydro-9-oxo-9H-xanthan-7-carboxylic acid, methyl ester;
4-(2,3-dimethoxy-benzylidene)-1,2,3,4-tetrahydro-9-oxo-9H-xanthen-7-carboxylic acid, methyl ester;
4-(2,5-dimethoxy-benzylidene)-1,2,3,4-tetrahydro-9-oxo-9H-xanthen-7-carboxylic acid, methyl ester;
4-(4-fluoro-benzylidene)-1,2,3,4-tetrahydro-9-oxo-9H-xanthen-7-carboxylic acid, methyl ester;
4-(2-chloro-benzylidene)-1,2,3,4-tetrahydro-9-oxo-9H-xanthen-7-carboxylic acid, methyl ester;
4-(3-chloro-benzylidene)-1,2,3,4-tetrahydro-9-oxo-9H-xanthen-7-carboxylic acid, methyl ester;
4-(3,4-dimethoxy-benzylidene)-1,2,3,4-tetrahydro-9-oxo-9H-xanthen-7-carboxylic acid, methyl ester;
4-(2,4-dimethoxy-benzylidene)-1,2,3,4-tetrahydro-9-oxo-9H-xanthen-7-carboxylic acid, methyl ester;
4-(2-methoxy-3-ethoxy-benzylidene)-1,2,3,4-tetrahydro-9-oxo-9H-xanthen-7-carboxylic acid, methyl ester;
4-(3,4,5-trimethoxy-benzylidene)-1,2,3,4-tetrahydro-9-oxo-9H-xanthen-7-carboxylic acid, methyl ester;
4-(2-thenylidene)-1,2,3,4-tetrahydro-9-oxo-9H-xanthen-7-carboxylic acid, methyl ester;
4-[(3-pyridyl)-methylene]-1,2,3,4-tetrahydro-9-oxo-9H-xanthen-7-carboxylic acid, methyl ester;
4-[(2-pyridyl)-methylene]-1,2,3,4-tetrahydro-9-oxo-9H-xanthen-7-carboxylic acid, methyl ester;
4-(4-chloro-benzylidene)-1,2,3,4-tetrahydro-9-oxo-9H-xanthen-7-carboxylic acid, methyl ester; and
4-(2,6-dichloro-benzylidene)-1,2,3,4-tetrahydro-9-oxo-9H-xanthen-7-carboxylic acid, methyl ester.

EXAMPLE 9

4-benzylidene-1,2,3,4-tetrahydro-9-oxo-9H-xanthen-7-carboxylic acid, methyl ester (1.2 g) was hydrolized by treatment with 1% KOH in 95% ethanol (19.5 ml) at reflux temperature for 15 minutes. After cooling and acidification with 37% HCl the precipitate was filtered and washed with methanol and then with water to give 1 g of 4-benzylidene-1,2,3,4-tetrahydro-9-oxo-9H-xanthen-7-carboxylic acid, m.p. 284°–286° C., NMR (CF$_3$COOD) δppm: 2.12 (m) (2H, C-2 protons), 3.13 (m) (4H, C-1 and C-3 protons), 7.64 (m) (5H, phenyl protons), 8.14 (d) (1H, C-5 proton), 8.43 (bs) (1H, =CH—), 8.88 (dd) (1H, C-6 proton), 9.38 (d) (1H, C-8 proton).

By proceeding analogously the following compounds were prepared:
4-(2-methyl-benzylidene)-1,2,3,4-tetrahydro-9-oxo-9H-xanthen-7-carboxylic acid, m.p. 290°–292° C.;
4-(3-methyl-benzylidene)-1,2,3,4-tetrahydro-9-oxo-9H-xanthen-7-carboxylic acid;
4-(4-methyl-benzylidene)-1,2,3,4-tetrahydro-9-oxo-9H-xanthen-7-carboxylic acid;
4-(2-methoxy-benzylidene)-1,2,3,4-tetrahydro-9-oxo-9H-xanthen-7-carboxylic acid;
4-(3-methoxy-benzylidene)-1,2,3,4-tetrahydro-9-oxo-9H-xanthen-7-carboxylic acid;
4-(4-methoxy-benzylidene)-1,2,3,4-tetrahydro-9-oxo-9H-xanthen-7-carboxylic acid;
4-(2-ethoxy-benzylidene)-1,2,3,4-tetrahydro-9-oxo-9H-xanthen-7-carboxylic acid;
4-(3-ethoxy-benzylidene)-1,2,3,4-tetrahydro-9-oxo-9H-xanthen-7-carboxylic acid;
4-(4-ethoxy-benzylidene)-1,2,3,4-tetrahydro-9-oxo-9H-xanthen-7-carboxylic acid;
4-(2,5-dimethyl-benzylidene)-1,2,3,4-tetrahydro-9-oxo-9H-xanthen-7-carboxylic acid;
4-(2,3-dimethoxy-benzylidene)-1,2,3,4-tetrahydro-9-oxo-9H-xanthen-7-carboxylic acid;
4-(2,5-dimethoxy-benzylidene)-1,2,3,4-tetrahydro-9-oxo-9H-xanthen-7-carboxylic acid;
4-(4-fluoro-benzylidene)-1,2,3,4-tetrahydro-9-oxo-9H-xanthen-7-carboxylic acid;
4-(2-chloro-benzylidene)-1,2,3,4-tetrahydro-9-oxo-9H-xanthen-7-carboxylic acid;
4-(3-chloro-benzylidene)-1,2,3,4-tetrahydro-9-oxo-9H-xanthen-7-carboxylic acid;
4-(2,4-dimethoxy-benzylidene)-1,2,3,4-tetrahydro-9-oxo-9H-xanthen-7-carboxylic acid;
4-(3,4-dimethoxy-benzylidene)-1,2,3,4-tetrahydro-9-oxo-9H-xanthen-7-carboxylic acid;
4-(2-methoxy-3-ethoxy-benzylidene)-1,2,3,4-tetrahydro-9-oxo-9H-xanthen-7-carboxylic acid;
4-(3,4,5-trimethoxy-benzylidene)-1,2,3,4-tetrahydro-9-oxo-9H-xanthen-7-carboxylic acid;
4-(2-thenylidene)-1,2,3,4-tetrahydro-9-oxo-9H-xanthen-7-carboxylic acid;
4-[(3-pyridyl)-methylene]-1,2,3,4-tetrahydro-9-oxo-9H-xanthen-7-carboxylic acid;
4-[(2-pyridyl)-methylene]-1,2,3,4-tetrahydro-9-oxo-9H-xanthen-7-carboxylic acid;
4-(4-chloro-benzylidene)-1,2,3,4-tetrahydro-9-oxo-9H-xanthen-7-carboxylic acid; and
4-(2,6-dichloro-benzylidene)-1,2,3,4-tetrahydro-9-oxo-9H-xanthen-7-carboxylic acid.

EXAMPLE 10

3-(2-methyl-benzylidene)-1,2,3,9-tetrahydro-9-oxo-cyclopenta[b][1]benzopyran-7-carboxylic acid (1.5 g) was reacted with thionyl chloride (10 ml) in dioxane (80 ml) at the reflux temperature for 4 hours, then the mixture was evaporated in vacuo to dryness.

The residue was dissolved in dioxane (60 ml) and reacted with 2-(diethylamino)-ethanol (1.5 g) at room temperature for 20 hours. After concentration in vacuo to a small volume, the residue was diluted with ice water and extracted with ethyl acetate after alkalinization with Na$_2$CO$_3$. The organic solution was evaporated in vacuo to dryness: crystallization of the residue from CH$_2$Cl$_2$-isopropyl ether gave 0.8 g of 3-(2-methyl-benzylidene)-1,2,3,9-tetrahydro-9-oxo-cyclopenta[b][1]benzopyran-7-carboxylic acid, 2-(diethylamino)-ethyl ester, m.p. 119°–120° C.

By proceeding analogously the following compounds were prepared:
3-(2-methyl-benzylidene)-1,2,3,9-tetrahydro-9-oxo-cyclopenta[b][1]benzopyran-7-carboxylic acid, 2-(dimethylamino)-ethyl ester;
3-(2-methoxy-benzylidene)-1,2,3,9-tetrahydro-9-oxo-cyclopenta[b][1]benzopyran-7-carboxylic acid, 2-(dimethylamino)-ethyl ester;
3-(3-methyl-benzylidene)-1,2,3,9-tetrahydro-9-oxo-cyclopenta[b][1]benzopyran-7-carboxylic acid, 2-(diethylamino)-ethyl ester;
3-(4-methyl-benzylidene)-1,2,3,9-tetrahydro-9-oxo-cyclopenta[b][1]benzopyran-7-carboxylic acid, 2-(diethylamino)-ethyl ester;
3-(2-methoxy-benzylidene)-1,2,3,9-tetrahydro-9-oxo-cyclopenta[b][1]benzopyran-7-carboxylic acid, 2-(diethylamino)-ethyl ester;

3-(3-methoxy-benzylidene)-1,2,3,9-tetrahydro-9-oxo-cyclopenta[b][1]benzopyran-7-carboxylic acid, 2-(diethylamino)-ethyl ester;

3-(4-methoxy-benzylidene)-1,2,3,9-tetrahydro-9-oxo-cyclopenta[b][1]benzopyran-7-carboxylic acid, 2-(diethylamino)-ethyl ester;

3-(2,3-dimethoxy-benzylidene)-1,2,3,9-tetrahydro-9-oxo-cyclopenta[b][1]benzopyran-7-carboxylic acid, 2-(diethylamino)-ethyl ester;

3-(2,5-dimethoxy-benzylidene)-1,2,3,9-tetrahydro-9-oxo-cyclopenta[b][1]benzopyran-7-carboxylic acid, 2-(dieethylamino)-ethyl ester;

3-(2,5-dimethyl-benzylidene)-1,2,3,9-tetrahydro-9-oxo-cyclopenta[b][1]benzopyran-7-carboxylic acid, 2-(diethylamino)-ethyl ester;

3-(2-ethoxy-benzylidene)-1,2,3,9-tetrahydro-9-oxo-cyclopenta[b][1]benzopyran-7-carboxylic acid, 2-(diethylamino)-ethyl ester;

3-(3-ethoxy-benzylidene)-1,2,3,9-tetrahydro-9-oxo-cyclopenta[b][1]benzopyran-7-carboxylic acid, 2-(diethylamino)-ethyl ester;

3-(4-ethoxy-benzylidene)-1,2,3,9-tetrahydro-9-oxo-cyclopenta[b][1]benzopyran-7carboxylic acid, 2-(diethylamino)-ethyl ester;

4-(2-methoxy-benzylidene)-1,2,3,4-tetrahydro-9-oxo-9H-xanthen-7-carboxylic acid, 2-(diethylamino)-ethyl ester;

4-(2-methyl-benzylidene)-1,2,3,4-tetrahydro-9-oxo-9H-xanthen-7-carboxylic acid, 2-(diethylamino)-ethyl ester;

3-benzylidene-1,2,3,9-tetrahydro-9-oxo-cyclopenta[b][1]benzopyran-7-carboxylic acid, 2-(diethylamino)-ethyl ester;

3-benzylidene-1,2,3,9-tetrahydro-9-oxo-cyclopenta[b][1]benzopyran-7-carboxylic acid, 2-(dimethylamino)-ethyl ester;

3-(4-chloro-benzylidene)-1,2,3,9-tetrahydro-9-oxo-cyclopenta[b][1]benzopyran-7-carboxylic acid, 2-(diethylamino)-ethyl ester;

3-(2,6-dichloro-benzylidene)-1,2,3,9-tetrahydro-9-oxo-cyclopenta[b][1]benzopyran-7-carboxylic acid, 2-(diethylamino)-ethyl ester;

3-(2-methoxy-3-ethoxy-benzylidene)-1,2,3,9-tetrahydro-9-oxo-cyclopenta[b][1]benzopyran-7-carboxylic acid, 2-(diethylamino)-ethyl ester; and 4-benzylidene-1,2,3,4-tetrahydro-9-oxo-9H-xanthen-7-carboxylic acid, 2-(diethylamino)-ethyl ester.

EXAMPLE 11

3-(2-methyl-benzylidene)-1,2,3,9-tetrahydro-9-oxo-cyclopenta[b][1]benzopyran-7-carboxylic acid (2.4 g) was reacted with thionyl chloride (14 ml) in dioxane (110 ml) at the reflux temperature for 4 hours, then the mixture was evaporated in vacuo to dryness.

The residue was dissolved in dioxane (85 ml) and reacted with excess of ammonia solution in dioxane (20 ml) under stirring at room temperature for 30 minutes. After concentration in vacuo, the residue was diluted with ice water and the precipitate was filtered and washed with water until neutral. After desiccation in vacuo, the obtained 3-(2-methyl-benzylidene)-1,2,3,9-tetrahydro-9-oxo-cyclopenta[b][1]benzopyran-7-carboxamide m.p. 293°-295° C. (2.1 g) was treated with p-toluenesulphonyl chloride (3.8 g) in pyridine (4 ml) and dimethylformamide (15 ml) at 80° C. for 6 hours. After cooling and dilution with ice water, the precipitate was filtered and washed with water until neutral: crystallization from CH$_2$Cl$_2$-isopropyl ether gave 7-cyano-3-(2-methyl-benzylidene)-1,2,3,9-tetrahydro-cyclopenta[b][1]benzopyran-9-one m.p. 260°-262° C. (1.6 g), which was reacted with sodium azide (3.3 g) and ammonium chloride (2.7 g) in dimethylformamide (15 ml) at 90° C. for 4 hours.

After cooling, dilution with ice water and acidification with 37% HCl, the precipitate was filtered and washed with water until neutral. Crystallization from CHCl$_3$-ethanol gave 1 g of 3-(2-methyl-benzylidene)-7-(1H-tetrazol-5-yl)-1,2,3,9-tetrahydro-cyclopenta[b][1]benzopyran-9-one, m.p. 300°-307° C. dec., NMR (CDCl$_3$+CF$_3$COOD) δppm: 2.57 (s) (3H, CH$_3$), 3.30 (m) (4H, C-1 and C-2 protons), 7.37 (m) and 7.64 (m) (3H and 1H, phenyl protons), 7.99 (t) (1H, =CH—), 8.11 (d) (1H, C-5 proton), 8.68 (dd) (1H, C-6 proton), 9.16 (d) (1H, C-8 proton).

By proceeding analogously the following compounds were prepared:

3-(3-methyl-benzylidene)-7-(1H-tetrazol-5-yl)-1,2,3,9-tetrahydro-cyclopenta[b][1]benzopyran-9-one;

3-(4-methyl-benzylidene)-7-(1H-tetrazol-5-yl)-1,2,3,9-tetrahydro-cyclopenta[b][1]benzopyran-9-one;

3-(2-methoxy-benzylidene)-7-(1H-tetrazol-5-yl)-1,2,3,9-tetrahydro-cyclopenta[b][1]benzopyran-9-one;

3-(3-methoxy-benzylidene)-7-(1H-tetrazol-5-yl)-1,2,3,9-tetrahydro-cyclopenta[b][1]benzopyran-9-one;

3-(4-methoxy-benzylidene)-7-(1H-tetrazol-5-yl)-1,2,3,9-tetrahydro-cyclopenta[b][1]benzopyran-9-one;

3-(4-ethoxy-benzylidene)-7-(1H-tetrazol-5-yl)-1,2,3,9-tetrahydro-cyclopenta[b][1]benzopyran-9-one;

3-(2,3-dimethoxy-benzylidene)-7-(1H-tetrazol-5-yl)-1,2,3,9-tetrahydro-cyclopenta[b][1]benzopyran-9-one;

3-(2,5-dimethoxy-benzylidene)-7-(1H-tetrazol-5-yl)-1,2,3,9-tetrahydro-cyclopenta[b][1]benzopyran-9-one;

3-benzylidene-7-(1H-tetrazol-5-yl)-1,2,3,9-tetrahydro-cyclopenta[b][1]benzopyran-9-one;

3-(2,6-dichloro-benzylidene)-7-(1H-tetrazol-5-yl)-1,2,3,9-tetrahydro-cyclopenta[b][1]benzopyran-9-one;

3-(4-chloro-benzylidene)-7-(1H-tetrazol-5-yl)-1,2,3,9-tetrahydro-cyclopenta[b][1]benzopyran-9-one;

3-(2,5-dimethyl-benzylidene)-7-(1H-tetrazol-5-yl)-1,2,3,9-tetrahydro-cyclopenta[b][1]benzopyran-9-one;

3-(3-ethoxy-benzylidene)-7-(1H-tetrazol-5-yl)-1,2,3,9-tetrahydro-cyclopenta[b][1]benzopyran-9-one;

3-(2-methoxy-3-ethoxy-benzylidene)-7-(1H-tetrazol-5-yl)-1,2,3,9-tetrahydro-cyclopenta[b][1]benzopyran-9-one; and 3-(4-fluoro-benzylidene)-7-(1H-tetrazol-5-yl)-1,2,3,9-tetrahydro-cyclopenta[b][1]benzopyran-9-one.

EXAMPLE 12

6-N-acetylamino-1,2,3,9-tetrahydro-cyclopenta[b][1]benzopyran-9-one, m.p. 275°-282° C. dec. (9 g), was reacted with benzaldehyde (5.9 g) in methanol (270 ml) in the presence of sodium methylate (4 g) under stirring at 60° C. for 15 hours. After cooling the precipitate was filtered and washed with methanol and then with water until neutral: it was found to be a mixture of the compounds 6-N-acetylamino-3-benzylidene-1,2,3,9-tetrahydro-cyclopenta[b][1]benzopyran-9-one, m.p. 243°-245° C., and 6-N-acetylamino-3-(α-hydroxy-benzyl)-1,2,3,9-tetrahydro-cyclopenta[b][1]benzopyran-9-one, m.p. 282°-283° C., which were identified on a sample after separation over a flash column using chloroform:e- thanol=93:7 as eluent. The mixture (8.5 g), without separation of the components, was suspended under stirring in 37% HCl (85 ml) and heated at 80° C. for 2 hours. After cooling, dilution with ice water and neutralization with NaOH, the precipitate was filtered and washed with water: crystallization from chloroform-methanol gave 5.9 g of 6-amino-3-benzylidene-1,2,3,9-tetrahydro-cyclopenta[b][1]benzopyran-9-one, m.p. 282°–285° C., NMR (DMSO d6) δppm: 2.6–3.1 (m) (4H, C-1 and C-2 protons), 6.28 (bs), (2H, —NH$_2$), 6.62 (m) (2H, C-5 and C-7 protons), 6.99 (bs) (1H, =CH—), 7.2–7.7 (m) (5H, phenyl protons), 7.71 (d) (1H, C-8 proton).

By proceeding analogously the following compounds were prepared:
7-amino-3-benzylidene-1,2,3,9-tetrahydro-cyclopenta[b][1]benzopyran-9-one, m.p. 245°–252° C. dec.;
7-amino-3-(2-methyl-benzylidene)-1,2,3,9-tetrahydro-cyclopenta[b][1]benzopyran-9-one;
7-amino-3-(2-methoxy-benzylidene)-1,2,3,9-tetrahydro-cyclopenta[b][1]benzopyran-9-one;
6-amino-3-(2-thenylidene)-1,2,3,9-tetrahydro-cyclopenta[b][1]benzopyran-9-one;
6-amino-3-[(2-pyridyl)-methylene]-1,2,3,9-tetrahydro-cyclopenta[b][1]benzopyran-9-one;
6-amino-3-[(3-pyridyl)-methylene]-1,2,3,9-tetrahydro-cyclopenta[b][1]benzopyran-9-one;
6-amino-3-(2-methyl-benzylidene)-1,2,3,9-tetrahydro-cyclopenta[b][1]benzopyran-9-one;
6-amino-3-(3-methyl-benzylidene)-1,2,3,9-tetrahydro-cyclopenta[b][1]benzopyran-9-one;
6-amino-3-(4-methyl-benzylidene)-1,2,3,9-tetrahydro-cyclopenta[b][1]benzopyran-9-one;
6-amino-3-(2-methoxy-benzylidene)-1,2,3,9-tetrahydro-cyclopenta[b][1]benzopyran-9-one;
6-amino-3-(3-methoxy-benzylidene)-1,2,3,9-tetrahydro-cyclopenta[b][1]benzopyran-9-one;
6-amino-3-(4-methoxy-benzylidene)-1,2,3,9-tetrahydro-cyclopenta[b][1]benzopyran-9-one;
6-amino-3-(2,6-dichloro-benzylidene)-1,2,3,9-tetrahydro-cyclopenta[b][1]benzopyran-9-one;
6-amino-3-(4-fluoro-benzylidene)-1,2,3,9-tetrahydro-cyclopenta[b][1]benzopyran-9-one;
6-amino-3-(2-chloro-benzylidene)-1,2,3,9-tetrahydro-cyclopenta[b][1]benzopyran-9-one;
6-amino-3-(2,3-dimethoxy-benzylidene)-1,2,3,9-tetrahydro-cyclopenta[b][1]benzopyran-9-one;
6-amino-3-(2,5-dimethoxy-benzylidene)-1,2,3,9-tetrahydro-cyclopenta[b][1]benzopyran-9-one;
6-amino-3-(3,4-dimethoxy-benzylidene)-1,2,3,9-tetrahydro-cyclopenta[b][1]benzopyran-9-one;
6-amino-3-(2-methoxy-3-ethoxy-benzylidene)-1,2,3,9-tetrahydro-cyclopenta[b][1]benzopyran-9-one;
6-amino-3-(3,4,5-trimethoxy-benzylidene)-1,2,3,9-tetrahydro-cyclopenta[b][1]benzopyran-9-one;
6-amino-3-(2,5-dimethyl-benzylidene)-1,2,3,9-tetrahydro-cyclopenta[b][1]benzopyran-9-one;
6-amino-3-(4-carboxy-benzylidene)-1,2,3,9-tetrahydro-cyclopenta[b][1]benzopyran-9-one;
7-amino-3-(4-carboxy-benzylidene)-1,2,3,9-tetrahydro-cyclopenta[b][1]benzopyran-9-one;
6-amino-3-(4-chloro-benzylidene)-1,2,3,9-tetrahydro-cyclopenta[b][1]benzopyran-9-one;
6-amino-3-(3-chloro-benzylidene)-1,2,3,9-tetrahydro-cyclopenta[b][1]benzopyran-9-one;
6-amino-3-(3-ethoxy-benzylidene)-1,2,3,9-tetrahydro-cyclopenta[b][1]benzopyran-9-one; and
6-amino-3-(4-ethoxy-benzylidene)-1,2,3,9-tetrahydro-cyclopenta[b][1]benzopyran-9-one.

EXAMPLE 13

6-amino-3-benzylidene-1,2,3,9-tetrahydro-cyclopenta[b][1]benzopyran-9-one (3.8 g), was reacted with ethyl oxalyl chloride (3.6 g) in dimethylacetamide (80 ml) in the presence of pyridine (3.8 ml) under stirring at room temperature for 2 hours. The reaction mixture was then diluted with ice water and the precipitate was filtered and washed with water: crystallization from CH$_2$Cl$_2$-isopropyl ether gave 3.5 g of N-(3-benzylidene-1,2,3,9-tetrahydro-9-oxo-cyclopenta[b][1]benzopyran-6-yl)-amino-oxoacetic acid, ethyl ester, m.p. 234°–235° C., which, was hydrolized by treatment with 1% KOH in 95% ethanol (175 ml) at room temperature for 30 minutes. After dilution with acetone (175 ml) the precipitate, N-(3-benzylidene-1,2,3,9-tetrahydro-9-oxo-cyclopenta[b][1]benzopyran-6-yl)-amino-oxoacetic acid, potassium salt, was filtered and dissolved in formic acid: dilution with water gave a precipitate which was filtered and washed with water until neutral. Crystallization from dimethylformamide-ethanol gave 2.9 g of N-(3-benzylidene-1,2,3,9-tetrahydro-9-oxo-cyclopenta[b][1]benzopyran-6-yl)-amino-oxoacetic acid, m.p. 253°–256° C., NMR (DMSO d$_6$) δppm: 2.80 (m) (2H, C-1 protons), 3.15 (m) (2H, C-2 protons), 7.23 (bs) (1H, =C—), 7.30–7.55 (m) (3H) and 7.65 (bd) (2H) (phenyl protons), 7.78 (dd) (1H, C-7 proton), 8.03 (d) (1H, C-8 proton), 8.32 (d) (1H, C-5 proton), 11.20 (bs) (1H, —NH—).

By proceeding analogously the following compounds were prepared:
N-[3-(2-methyl-benzylidene)-1,2,3,9-tetrahydro-9-oxo-cyclopenta[b][1]benzopyran-6-yl]-amino-oxoacetic acid, ethyl ester;
N-[3-(3-methyl-benzylidene)-1,2,3,9-tetrahydro-9-oxo-cyclopenta[b][1]benzopyran-6-yl]-amino-oxoacetic acid, ethyl ester;
N-[3-(4-methyl-benzylidene)-1,2,3,9-tetrahydro-9-oxo-cyclopenta[b][1]benzopyran-6-yl]-amino-oxoacetic acid, ethyl ester;
N-[3-(2-methoxy-benzylidene)-1,2,3,9-tetrahydro-9-oxo-cyclopenta[b][1]benzopyran-6-yl]-amino-oxoacetic acid, ethyl ester;
N-[3-(3-methoxy-benzylidene)-1,2,3,9-tetrahydro-9-oxo-cyclopenta[b][1]benzopyran-6-yl]-amino-oxoacetic acid, ethyl ester;
N-[3-(4-methoxy-benzylidene)-1,2,3,9-tetrahydro-9-oxo-cyclopenta[b][1]benzopyran-6-yl]-amino-oxoacetic acid, ethyl ester;
N-[3-(4-fluoro-benzylidene)-1,2,3,9-tetrahydro-9-oxo-cyclopenta[b][1]benzopyran-6-yl]-amino-oxoacetic acid, ethyl ester;
N-[3-(3-ethoxy-benzylidene)-1,2,3,9-tetrahydro-9-oxo-cyclopenta[b][1]benzopyran-6-yl]-amino-oxoacetic acid, ethyl ester;
N-[3-(2,3-dimethoxy-benzylidene)-1,2,3,9-tetrahydro-9-oxo-cyclopenta[b][1]benzopyran-6-yl]-amino-oxoacetic acid, ethyl ester;
N-[3-(3,4-dimethoxy-benzylidene)-1,2,3,9-tetrahydro-9-oxo-cyclopenta[b][1]benzopyran-6-yl]-amino-oxoacetic acid, ethyl ester;
N-[3-(2,5-dimethoxy-benzylidene)-1,2,3,9-tetrahydro-9-oxo-cyclopenta[b][1]benzopyran-6-yl]-amino-oxoacetic acid, ethyl ester;

N-[3-(2,6-dichloro-benzylidene)-1,2,3,9-tetrahydro-9-oxo-cyclopenta[b][1]benzopyran-6-yl]-amino-oxoacetic acid, ethyl ester;

N-[3-(2-chloro-benzylidene)-1,2,3,9-tetrahydro-9-oxo-cyclopenta[b][1]benzopyran-6-yl]-amino-oxoacetic acid, ethyl ester;

N-[3-(2,5-dimethyl-benzylidene)-1,2,3,9-tetrahydro-9-oxo-cyclopenta[b][1]benzopyran-6-yl]-amino-oxoacetic acid, ethyl ester;

N-[3-(4-chloro-benzylidene)-1,2,3,9-tetrahydro-9-oxo-cyclopenta[b][1]benzopyran-6-yl]-amino-oxoacetic acid, ethyl ester;

N-(3-benzylidene-1,2,3,9-tetrahydro-9-oxo-cyclopenta[b][1]benzopyran-7-yl)-amino-oxoacetic acid, ethyl ester; m.p. 263°–266° C.;

N-[3-(4-ethoxy-benzylidene)-1,2,3,9-tetrahydro-9-oxocyclopenta[b][1]benzopyran-6-yl]-amino-oxoacetic acid, ethyl ester;

N-[3-(2-methoxy-benzylidene)-1,2,3,9-tetrahydro-9-oxo-cyclopenta[b][1]benzopyran-7-yl]-amino-oxoacetic acid, ethyl ester;

N-[3-(2-thenylidene)-1,2,3,9-tetrahydro-9-oxo-cyclopenta[b][1]benzopyran-6-yl]-amino-oxoacetic acid, ethyl ester;

N-{3-[(2-pyridyl)-methylene]-1,2,3,9-tetrahydro-9-oxo-cyclopenta[b][1]benzopyran-6-yl}-amino-oxoacetic acid, ethyl ester;

N-{3-[(3-pyridyl)-methylene]-1,2,3,9-tetrahydro-9-oxo-cyclopenta[b][1]benzopyran-6-yl}-amino-oxoacetic acid, ethyl ester;

N-[3-(2-methyl-benzylidene)-1,2,3,9-tetrahydro-9-oxo-cyclopenta[b][1]benzopyran-6-yl]-amino-oxoacetic acid;

N-[3-(3-methyl-benzylidene)-1,2,3,9-tetrahydro-9-oxo-cyclopenta[b][1]benzopyran-6-yl]-amino-oxoacetic acid;

N-[3-(4-methyl-benzylidene)-1,2,3,9-tetrahydro-9-oxo-cyclopenta[b][1]benzopyran-6-yl]-amino-oxoacetic acid;

N-[3-(2-methoxy-benzylidene)-1,2,3,9-tetrahydro-9-oxo-cyclopenta[b][1]benzopyran-6-yl]-amino-oxoacetic acid;

N-[3-(3-methoxy-benzylidene)-1,2,3,9-tetrahydro-9-oxo-cyclopenta[b][1]benzopyran-6-yl]-amino-oxoacetic acid;

N-[3-(4-methoxy-benzylidene)-1,2,3,9-tetrahydro-9-oxo-cyclopenta[b][1]benzopyran-6-yl]-amino-oxoacetic acid;

N-[3-(4-fluoro-benzylidene)-1,2,3,9-tetrahydro-9-oxo-cyclopenta[b][1]benzopyran-6-yl]-amino-oxoacetic acid;

N-[3-(4-chloro-benzylidene)-1,2,3,9-tetrahydro-9-oxo-cyclopenta[b][1]benzopyran-6-yl]-amino-oxoacetic acid;

N-[3-(2-ethoxy-benzylidene)-1,2,3,9-tetrahydro-9-oxo-cyclopenta[b][1]benzopyran-6-yl]-amino-oxoacetic acid;

N-[3-(2,3-dimethoxy-benzylidene)-1,2,3,9-tetrahydro-9-oxo-cyclopenta[b][1]benzopyran-6-yl]-amino-oxoacetic acid;

N-[3-(3,4-dimethoxy-benzylidene)-1,2,3,9-tetrahydro-9-oxo-cyclopenta[b][1]benzopyran-6-yl]-amino-oxoacetic acid;

N-[3-(2,5-dimethoxy-benzylidene)-1,2,3,9-tetrahydro-9-oxo-cyclopenta[b][1]benzopyran-6-yl]-amino-oxoacetic acid;

N-[3-(3,4,5-trimethoxy-benzylidene)-1,2,3,9-tetrahydro-9-oxo-cyclopenta[b][1]benzopyran-6-yl]-amino-oxoacetic acid;

N-[3-(2-chloro-benzylidene)-1,2,3,9-tetrahydro-9-oxo-cyclopenta[b][1]benzopyran-6-yl]-amino-oxoacetic acid;

N-[3-(2,5-dimethyl-benzylidene)-1,2,3,9-tetrahydro-9-oxo-cyclopenta[b][1]benzopyran-6-yl]-amino-oxoacetic acid;

N-[3-(3,4-methylenedioxy-benzylidene)-1,2,3,9-tetrahydro-9-oxo-cyclopenta[b][1]benzopyran-6-yl]-amino-oxoacetic acid;

N-(3-benzylidene-1,2,3,9-tetrahydro-9-oxo-cyclopenta[b][1]benzopyran-7-yl)-amino-oxoacetic acid, m.p. 300°–305° C.;

N-[3-(2,6-dichloro-benzylidene)-1,2,3,9-tetrahydro-9-oxo-cyclopenta[b][1]benzopyran-6-yl]-amino-oxoacetic acid;

N-[3-(2-methyl-benzylidene)-1,2,3,9-tetrahydro-9-oxo-cyclopenta[b][1]benzopyran-7-yl]-amino-oxoacetic acid;

N-[3-(2-methoxy-benzylidene)-1,2,3,9-tetrahydro-9-oxo-cyclopenta[b][1]benzopyran-7-yl]-amino-oxoacetic acid;

N-[3-(2-thenylidene)-1,2,3,9-tetrahydro-9-oxo-cyclopenta[b][1]benzopyran-6-yl]-amino-oxoacetic acid;

N-{3-[(2-pyridyl)-methylene]-1,2,3,9-tetrahydro-9-oxo-cyclopenta[b][1]benzopyran-6-yl}-amino-oxoacetic acid;

N-{3-[(3-pyridyl)-methylene]-1,2,3,9-tetrahydro-9-oxo-cyclopenta[b][1]benzopyran-6-yl}-amino-oxoacetic acid;

3-benzylidene-6-N-methoxycarbonyl-amino-1,2,3,9-tetrahydro-cyclopenta[b][1]benzopyran-9-one;

3-benzylidene-6-N-ethoxycarbonyl-amino-1,2,3,9-tetrahydro-cyclopenta[b][1]benzopyran-9-one;

3-benzylidene-7-N-methoxycarbonyl-amino-1,2,3,9-terahydro-cyclopenta[b][1]benzopyran-9-one;

3-benzylidene-7-N-ethoxycarbonyl-amino-1,2,3,9-tetrahydro-cyclopenta[b][1]benzopyran-9-one;

N-[3-(2-methoxy-3-ethoxy-benzylidene)-1,2,3,9-tetrahydro-9-oxo-cyclopenta[b][1]benzopyran-6-yl]-amino-oxoacetic acid;

N-[3-(3-chloro-benzylidene)-1,2,3,9-tetrahydro-9-oxo-cyclopenta[b][1]benzopyran-6-yl]-amino-oxoacetic acid;

N-[3-(3-ethoxy-benzylidene)-1,2,3,9-tetrahydro-9-oxo-cyclopenta[b][1]benzopyran-6yl]-amino-oxoacetic acid;

N-[3-(4-ethoxy-benzylidene)-1,2,3,9-tetrahydro-9-oxo-cyclopenta[b][1]benzopyran-6-yl]-amino-oxoacetic acid;

N-[3-(2,4,-dimethyl-benzylidene)-1,2,3,9-tetrahydro-9-oxo-cyclopenta[b][1]benzopyran-6-yl]-amino-oxoacetic acid;

N-[3-(3-methoxy-2-ethoxy-benzylidene)-1,2,3,9-tetrahydro-9-oxo-cyclopenta[b][1]benzopyran-6-yl]-amino-oxoacetic acid;

N-[3-(2,4-dichloro-benzylidene)-1,2,3,9-tetrahydro-9-oxo-cyclopenta[b][1]benzopyran-6-yl]-amino-oxoacetic acid; and N-[3-(3,4-dichloro-benzylidene)-1,2,3,9-tetrahydro-9-oxo-cyclopenta[a][1]benzopyran-6-yl]-amino-oxoacetic acid.

EXAMPLE 14

By proceeding according to Example 13, using suitable acyl chlorides, the following compounds were prepared:

N-(3-benzylidene-1,2,3,9-tetrahydro-9-oxo-cyclopenta[b][1]benzopyran-6-yl)-aminocarbonyl-acetic acid, ethyl ester;

N-(3-benzylidene-1,2,3,9-tetrahydro-9-oxo-cyclopenta[b][1]benzopyran-6-yl)-aminocarbonyl-acetic acid;

3-[N-(3-benzylidene-1,2,3,9-tetrahydro-9-oxo-cyclopenta[b][1]benzopyran-6-yl)-aminocarbonyl]-propanoic acid, methyl ester;

3-[N-(3-benzylidene-1,2,3,9-tetrahydro-9-oxo-cyclopenta[b][1]benzopyran-6-yl)-aminocarbonyl]-propanoic acid;

(E)-3-[N-(3-benzylidene-1,2,3,9-tetrahydro-9-oxo-cyclopenta[b][1]benzopyran-6-yl)-aminocarbonyl]-2-propenoic acid, ethyl ester, m.p. 291°–293° C.;

(E)-3-[N-(3-benzylidene-1,2,3,9-tetrahydro-9-oxo-cyclopenta[b][1]benzopyran-6-yl)-aminocarbonyl]-2-propenoic acid, m.p. 340°–350° C. dec.;

(E)-3-{N-[3-(2-methoxy-3-ethoxy-benzylidene)-1,2,3,9-tetrahydro-9-oxo-cyclopenta[b][1]benzopyran-6-yl]-aminocarbonyl}-2-propenoic acid;

(E)-3-{N-[3-(2-methyl-benzylidene)-1,2,3,9-tetrahydro-9-oxo-cyclopenta[b][1]benzopyran-6-yl]-aminocarbonyl}-2-propenoic acid;

(E)-3-{N-[3-(4-fluoro-benzylidene)-1,2,3,9-tetrahydro-9-oxo-cyclopenta[b][1]benzopyran-6-yl]-aminocarbonyl}-2-propenoic acid;

(E)-3-{N-[3-(2-chloro-benzylidene)-1,2,3,9-tetrahydro-9-oxo-cyclopenta[b][1]benzopyran-6-yl]-aminocarbonyl}-2-propenoic acid;

(E)-3-[N-(3-benzylidene-1,2,3,9-tetrahydro-9-oxo-cyclopenta[b][1]benzopyran-7-yl)-aminocarbonyl]-2-propenoic acid;

3-[N-(3-benzylidene-1,2,3,9-tetrahydro-9-oxo-cyclopenta[b][1]benzopyran-6-yl)-aminocarbonyl]-benzoic acid, m.p. 370°–373° C.;

4-[N-(3-benzylidene-1,2,3,9-tetrahydro-9-oxo-cyclopenta[b][1]benzopyran-6-yl)-aminocarbonyl]-benzoic acid;

(E)-3-{N-[3-(3-methyl-benzylidene)-1,2,3,9-tetrahydro-9-oxo-cyclopenta[b][1]benzopyran-6-yl]-aminocarbonyl}-2-propenoic acid;

(E)-3-{N-[3-(4-chloro-benzylidene)-1,2,3,9-tetrahydro-9-oxo-cyclopenta[b][1]benzopyran-6-yl]-aminocarbonyl}-2-propenoic acid;

(E)-3-{N-[3-(2,6-dichloro-benzylidene)-1,2,3,9-tetrahydro-9-oxo-cyclopenta[b][1]benzopyran-6-yl]-aminocarbonyl}-2-propenoic acid;

(E)-3-{N-[3-(2,5-dimethyl-benzylidene)-1,2,3,9-tetrahydro-9-oxo-cyclopenta[b][1]benzopyran-6-yl]-aminocarbonyl}-2-propenoic acid;

(E)-3-{N-[3-(2,5-dimethoxy-benzylidene)-1,2,3,9-tetrahydro-9-oxo-cyclopenta[b][1]benzopyran-6-yl]-aminocarbonyl}-2-propenoic acid;

(E)-3-{N-[3-(2,3-dimethoxy-benzylidene)-1,2,3,9-tetrahydro-9-oxo-cyclopenta[b][1]benzopyran-6-yl]-aminocarbonyl}-2-propenoic acid;

(E)-3-{N-[3-(4-methoxy-benzylidene)-1,2,3,9-tetrahydro-9-oxo-cyclopenta[b][1]benzopyran-6-yl]-aminocarbonyl}-2-propenoic acid;

(E)-3-{N-[3-(4-ethoxy-benzylidene)-1,2,3,9-tetrahydro-9-oxo-cyclopenta[b][1]benzopyran-6-yl]-aminocarbonyl}-2-propenoic acid;

(E)-3-{N-[3-(4-methyl-benzylidene)-1,2,3,9-tetrahydro-9-oxo-cyclopenta[b][1]benzopyran-6-yl]-aminocarbonyl}-2-propenoic acid;

(E)-3-{N-[3-(3-chloro-benzylidene)-1,2,3,9-tetrahydro-9-oxo-cyclopenta[b][1]benzopyran-6-yl]-aminocarbonyl}-2-propenoic acid;

(E)-3-{N-[3-(2-ethoxy-benzylidene)-1,2,3,9-tetrahydro-9-oxo-cyclopenta[b][1]benzopyran-6-yl]-aminocarbonyl}-2propenoic acid;

(E)-3-{N-[3-(2-methoxy-benzylidene)-1,2,3,9-tetrahydro-9-oxo-cyclopenta[b][1]benzopyran-6-yl]-aminocarbonyl}-2-propenoic acid;

(E)-3-{N-[3-(3-methoxy-benzylidene)-1,2,3,9-tetrahydro-9-oxo-cyclopenta[b][1]benzopyran-6-yl]-aminocarbonyl}-2-propenoic acid; and (E)-3-{N-[3-(3-ethoxy-benzylidene)-1,2,3,9-tetrahydro-9-oxo-cyclopenta[b][1]benzopyran-6-yl]-aminocarbonyl}-2-propenoic acid.

EXAMPLE 15

6-amino-3-benzylidene-1,2,3,9-tetrahydro-cyclopenta[b][1]benzopyran-9-one (3 g) was reacted with maleic anhydride (4.55 g) in dioxane (90 ml) under stirring at the reflux temperature for 14 hours.

After cooling the precipitate was filtered and washed with tetrahydrofuran and then with water: crystallization from chloroform-ethanol gave 2.5 g of (Z)-3-[N-(3-benzylidene-1,2,3,9-tetrahydro-9-oxo-cyclopenta[b][1]benzopyran-6-yl)-aminocarbonyl]-2-propenoic acid, m.p. 230° C. dec.

By proceeding analogously the following compounds were prepared:

(Z)-3-{N-[3-(2-methyl-benzylidene)-1,2,3,9-tetrahydro-9-oxo-cyclopenta[b][1]benzopyran-6-yl]-aminocarbonyl}-2-propenoic acid;

(Z)-3-{N-[3-(3-methoxy-benzylidene)-1,2,3,9-tetrahydro-9-oxo-cyclopenta[b][1]benzopyran-6-yl]-aminocarbonyl}-2-propenoic acid;

(Z)-3-[N-(3-benzylidene-1,2,3,9-tetrahydro-9-oxo-cyclopenta[b][1]benzopyran-7-yl)-aminocarbonyl]-2-propenoic acid;

2-[N-(3-benzylidene-1,2,3,9-tetrahydro-9-oxo-cyclopenta[b][1]benzopyran-6-yl)-aminocarbonyl]-benzoic acid, m.p. 250° C. dec.;

2-[N-(3-benzylidene-1,2,3,9-tetrahydro-9-oxo-cyclopenta[b][1]benzopyran-7-yl)-aminocarbonyl]-benzoic acid;

(Z)-3-{N-[3-(3-methyl-benzylidene)-1,2,3,9-tetrahydro-9-oxo-cyclopenta[b][1]benzopyran-6-yl]-aminocarbonyl}-2-propenoic acid;

(Z)-3-{N-[3-(4-methoxy-benzylidene)-1,2,3,9-tetrahydro-9-oxo-cyclopenta[b][1]benzopyran-6-yl]-aminocarbonyl}-2-propenoic acid;

(Z)-3-{N-[3-(2-chloro-benzylidene)-1,2,3,9-tetrahydro-9-oxo-cyclopenta[b][1]benzopyran-6-yl]-aminocarbonyl}-2-propenoic acid;

(Z)-3-{N-[3-(2-methoxy-3-ethoxy-benzylidene)-1,2,3,9-tetrahydro-9-oxo-cyclopenta[b][1]benzopyran-6-yl]-aminocarbonyl}-2-propenoic acid;

(Z)-3-{N-[3-(4-chloro-benzylidene)-1,2,3,9-tetrahydro-9-oxo-cyclopenta[b][1]benzopyran-6-yl]-aminocarbonyl}-2-propenoic acid;

(Z)-3-{N-[3-(2,6-dichloro-benzylidene)-1,2,3,9-tetrahydro-9-oxo-cyclopenta[b][1]benzopyran-6-yl]-aminocarbonyl}-2-propenoic acid;

(Z)-3-{N-[3-(2,5-dimethyl-benzylidene)-1,2,3,9-tetrahydro-9-oxo-cyclopenta[b][1]benzopyran-6-yl]-aminocarbonyl}-2-propenoic acid;

(Z)-3-{N-[3-(2,3-dimethoxy-benzylidene)-1,2,3,9-tetrahydro-9-oxo-cyclopenta[b][1]benzopyran-6-yl]-aminocarbonyl}-2-propenoic acid;
(Z)-3-{N-[3-(4-ethoxy-benzylidene)-1,2,3,9-tetrahydro-9-oxo-cyclopenta[b][1]benzopyran-6-yl]-aminocarbonyl}-2-propenoic acid;
(Z)-3-{N-[3-(4-methyl-benzylidene)-1,2,3,9-tetrahydro-9-oxo-cyclopenta[b][1]benzopyran-6-yl]-aminocarbonyl}-2-propenoic acid;
(Z)-3-{N-[3-(2-methoxy-benzylidene)-1,2,3,9-tetrahydro-9-oxo-cyclopenta[b][1]benzopyran-6-yl]-aminocarbonyl}-2-propenoic acid;
(Z)-3-{N-[3-(3-chloro-benzylidene)-1,2,3,9-tetrahydro-9-oxo-cyclopenta[b][1]benzopyran-6-yl]-aminocarbonyl}-2-propenoic acid;
(Z)-3-{N-[3-(2-ethoxy-benzylidene)-1,2,3,9-tetrahydro-9-oxo-cyclopenta[b][1]benzopyran-6-yl]-aminocarbonyl}-2-propenoic acid;
(Z)-3-{N-[3-(4-fluoro-benzylidene)-1,2,3,9-tetrahydro-9-oxo-cyclopenta[b][1]benzopyran-6-yl]-aminocarbonyl}-2-propenoic acid;
(Z)-3-{N-[3-(2,5-dimethoxy-benzylidene)-1,2,3,9-tetrahydro-9-oxo-cyclopenta[b][1]benzopyran-6-yl]aminocarbonyl}-2-propenoic acid; and
(Z)-3-{N-[3-(3-ethoxy-benzylidene)-1,2,3,9-tetrahydro-9-oxo-cyclopenta[b][1]benzopyran-6-yl]-aminocarbonyl}-2-propenoic acid.

EXAMPLE 16

By proceeding according to Example 12, starting from 6-N-acetylamino-1,2,3,4-tetrahydro-9H-xanthen-9-one, the following compounds were prepared:
6-N-acetylamino-4-benzylidene-1,2,3,4-tetrahydro-9H-xanthen-9-one;
7-N-acetylamino-4-benzylidene-1,2,3,4-tetrahydro-9H-xanthen-9-one;
6-amino-4-benzylidene-1,2,3,4-tetrahydro-9H-xanthen-9-one;
7-amino-4-benzylidene-1,2,3,4-tetrahydro-9H-xanthen-9-one;
6-amino-4-(2-methyl-benzylidene)-1,2,3,4-tetrahydro-9H-xanthen-9-one;
6-amino-4-(2-methoxy-benzylidene)-1,2,3,4-tetrahydro-9H-xanthen-9-one;
7-amino-4-(2-methyl-benzylidene)-1,2,3,4-tetrahydro-9H-xanthen-9-one;
7-amino-4-(2-methoxy-benzylidene)-1,2,3,4-tetrahydro-9H-xanthen-9-one; and
6-amino-4-(4-carboxy-benzylidene)-1,2,3,4-tetrahydro-9H-xanthen-9-one.

EXAMPLE 17

By proceeding according to Example 13, starting from suitable amino-4-benzylidene-1,2,3,4-tetrahydro-9H-xanthen-9-ones, the following compounds were prepared:
N-(4-benzylidene-1,2,3,4-tetrahydro-9-oxo-9H-xanthen-6-yl)-amino-oxoacetic acid;
N-[4-(2-methyl-benzylidene)-1,2,3,4-tetrahydro-9-oxo-9H-xanthen-6-yl]-amino-oxoacetic acid;
N-[4-(2-methoxy-benzylidene)-1,2,3,4-tetrahydro-9-oxo-9H-xanthen-6-yl]-amino-oxoacetic acid;
N-(4-benzylidene-1,2,3,4-tetrahydro-9-oxo-9H-xanthen-7-yl)-amino-oxoacetic acid;
N-[4-(2-methyl-benzylidene)-1,2,3,4-tetrahydro-9-oxo-9H-xanthen-7-yl]-amino-oxoacetic acid;
N-[4-(2-methoxy-benzylidene)-1,2,3,4-tetrahydro-9-oxo-9H-xanthen-7-yl]-amino-oxoacetic acid;
4-benzylidene-6-N-ethoxycarbonyl-amino-1,2,3,4-tetrahydro-9H-xanthen-9-one; and
4-benzylidene-7-N-ethoxycarbonyl-amino-1,2,3,4-tetrahydro-9H-xanthen-9-one.

EXAMPLE 18

6-amino-3-benzylidene-1,2,3,9-tetrahydro-cyclopenta[b][1]benzopyran-9-one (2.3 g) was reacted with chloroacetyl chloride (1.35 g) in dimethylacetamide (100 ml) in the presence of pyridine (1.9 ml) at room temperature for 3 hours.

The reaction mixture was diluted with ice water and the precipitate was filtered and washed with water to give 3-benzylidene-6-N-chloroacetyl-amino-1,2,3,9-tetrahydro-cyclopenta[b][1]benzopyran-9-one, m.p. 308°–312° C. (2.3 g), which was reacted with morpholine (0.63 g) in dimethylacetamide (90 ml) in the presence of anhydrous potassium carbonate (1 g) under stirring at 60° C. for 4 hours. After cooling the precipitate was filtered and washed with water: crystallization from chloroform-ethanol gave 1.3 g of 3-benzylidene-6-N-morpholinoacetyl-amino-1,2,3,9-tetrahydro-cyclopenta[b][1]benzopyran-9-one, m.p. 163°–167° C. dec.

By proceeding analogously the following compounds were prepared:
3-(2-methyl-benzylidene)-6-N-morpholinoacetyl-amino-1,2,3,9-tetrahydro-cyclopenta[b][1]benzopyran-9-one;
3-(2-methoxy-benzylidene)-6-N-morpholinoacetyl-amino-1,2,3,9-tetrahydro-cyclopenta[b][1]benzopyran-9-one;
3-(2-methoxy-3-ethoxy-benzylidene)-6-N-morpholinoacetyl-amino-1,2,3,9-tetrahydro-cyclopenta[b][1]benzopyran-9-one
3-(4-ethoxy-benzylidene)-6-N-morpholinoacetyl-amino-1,2,3,9-tetrahydro-cyclopenta[b][1]benzopyran-9-one;
3-(2,3-dimethoxy-benzylidene)-6-N-morpholinoacetyl-amino-1,2,3,9-tetrahydro-cyclopenta[b][1]benzopyran-9-one;
3-benzylidene-6-N-piperidinoacetyl-amino-1,2,3,9-tetrahydro-cyclopenta[b][1]benzopyran-9-one;
3-(2-methyl-benzylidene)-6-N-piperidinoacetyl-amino-1,2,3,9-tetrahydro-cyclopenta[b][1]benzopyran-9-one;
3-(3-methoxy-benzylidene)-6-N-morpholinoacetyl-amino-1,2,3,9-tetrahydro-cyclopenta[b][1]benzopyran-9-one;
3-benzylidene-6-N-[(4-methyl-piperazin-1-yl)-acetyl]-amino-1,2,3,9-tetrahydro-cyclopenta[b][1]benzopyran-9-one;
3-(2-methyl-benzylidene)-6-N-[(4-methyl-piperazin-1-yl)-acetyl]-amino-1,2,3,9-tetrahydro-cyclopenta[b][1]benzopyran-9-one;
3-(2-methoxy-benzylidene)-6-N-[(4-methyl-piperazin-1-yl)-acetyl]-amino-1,2,3,9-tetrahydro-cyclopenta[b][1]benzopyran-9-one;
3-benzylidene-6-N-[(pyrrolidin-1-yl)-acetyl]-amino-1,2,3,9-tetrahydro-cyclopenta[b][1]benzopyran-9-one;
3-(4-methyl-benzylidene)-6-N-morpholinoacetyl-amino-1,2,3,9-tetrahydro-cyclopenta[b][1]benzopyran-9-one; 3-benzylidene-6-N-[(N,N-diethylamino)-acetyl]-amino-1,2,3,9-tetrahydro-cyclopenta[b][1]benzopyran-9-one;

3-benzylidene-6-N-[(N-isopropylamino)-acetyl]-amino-1,2,3,9-tetrahydro-cyclopenta[b][1]benzopyran-9-one;

3-(4-flfuoro-benzylidene)-6-N-morpholinoacetyl-amino-1,2,3,9-tetrahydro-cyclopenta[b][1]benzopyran-9-one;

3-(2-chloro-benzylidene)-6-N-morpholinoacetyl-amino-1,2,3,9-tetrahydro-cyclopenta[b][1]benzopyran-9-one;

3-(4-chloro-benzylidene)-6-N-morpholinoacetyl-amino-1,2,3,9-tetrahydro-cyclopenta[b][1]benzopyran-9-one;

3-(2,6-dichloro-benzylidene)-6-N-morpholinoacetyl-amino-1,2,3,9-tetrahydro-cyclopenta[b][1]benzopyran-9-one;

3-(3-methyl-benzylidene)-6-N-morpholinoacetyl-amino-1,2,3,9-tetrahydro-cyclopenta[b][1]benzopyran-9-one;

3-(3-chloro-benzylidene)-6-N-morpholinoacetyl-amino-1,2,3,9-tetrahydro-cyclopenta[b][1]benzopyran-9-one;

3-(2-ethoxy-benzylidene)-6-N-morpholinoacetyl-amino-1,2,3,9-tetrahydro-cyclopenta[b][1]benzopyran-9-one;

3-(3-ethoxy-benzylidene)-6-N-morpholinoacetyl-amino-1,2,3,9-tetrahydro-cyclopenta[b][1]benzopyran-9-one;

3-(4-methoxy-benzylidene)-6-N-morpholinoacetyl-amino-1,2,3,9-tetrahydro-cyclopenta[b][1]benzopyran-9-one; and 3-(2,5-dimethoxy-benzylidene)-6-N-morpholinoacetyl-amino-1,2,3,9-tetrahydro-cyclopenta[b][1]benzopyran-9-one.

EXAMPLE 19

By proceeding according to Examples 1, 5 and 6, starting from suitable 1,2,3,9-tetrahydro-cyclopenta[b][1]benzopyran-9-ones or 1,2,3,4-tetrahydro-9H-xanthen-9-ones, the following compounds were prepared:

3-benzylidene-6-hydroxy-1,2,3,9-tetrahydro-cyclopenta[b][1]benzopyran-9-one, m.p. 320°–325° C. dec.;

3-benzylidene-7-hydroxy-1,2,3,9-tetrahydro-cyclopenta[b][1]benzopyran-9-one, m.p. 321°–322° C.;

6-hydroxy-3-thenylidene-1,2,3,9-tetrahydro-cyclopenta[b][1]benzopyran-9-one;

7-hydroxy-3-thenylidene-1,2,3,9-tetrahydro-cyclopenta[b][1]benzopyran-9-one;

6-hydroxy-3-[(2-pyridyl)-methylene]-1,2,3,9-tetrahydro-cyclopenta[b][1]benzopyran-9-one;

7-hydroxy-3-[(2-pyridyl)-methylene]-1,2,3,9-tetrahydro-cyclopenta[b][1]benzopyran-9-one;

6-hydroxy-3-[(3-pyridyl)-methyl]-1,2,3,9-tetrahydro-cyclopenta[b][1]benzopyran-9-one;

7-hydroxy-3-[(3-pyridyl)-methylene]-1,2,3,9-tetrahydro-cyclopenta[b][1]benzopyran-9-one;

4-benzylidene-6-hydroxy-1,2,3,4-tetrahydro-9H-xanthen-9-one;

4-benzylidene-7-hydroxy-1,2,3,4-tetrahydro-9H-xanthen-9-one;

6-hydroxy-3-(2-methyl-benzylidene)-1,2,3,9-tetrahydro-cyclopenta[b][1]benzopyran-9-one;

6-hydroxy-3-(2-methoxy-benzylidene)-1,2,3,9-tetrahydro-cyclopenta[b][1]benzopyran-9-one;

7-hydroxy-3-(2-methyl-benzylidene)-1,2,3,9-tetrahydro-cyclopenta[b][1]benzopyran-9-one;

7-hydroxy-3-(2-methoxy-benzylidene)-1,2,3,9-tetrahydro-cyclopenta[b][1]benzopyran-9-one;

3-benzylidene-6-methoxy-1,2,3,9-tetrahydro-cyclopenta[b][1]benzopyran-9-one;

3-benzylidene-7-methoxy-1,2,3,9-tetrahydro-cyclopenta[b][1]benzopyran-9-one;

3-(4-carboxy-benzylidene)-6-hydroxy-1,2,3,9-tetrahydrocyclopenta[b][1]benzopyran-9-one;

3-(4-carboxy-benzylidene)-7-hydroxy-1,2,3,9-tetrahydro-cyclopenta[b][1]benzopyran-9-one;

3-benzylidene-6-chloro-1,2,3,9-tetrahydro-cyclopenta[b][1]benzopyran-9-one;

3-benzylidene-7-chloro-1,2,3,9-tetrahydro-cyclopenta[b][1]benzopyran-9-one;

3-benzylidene-6-methyl-1,2,3,9-tetrahydro-cyclopenta[b][1]benzopyran-9-one;

3-benzylidene-7-methyl-1,2,3,9-tetrahydro-cyclopenta[b][1]benzopyran-9-one;

4-benzylidene-6-hydroxy-1,2,3,4-tetrahydro-9H-xanthen-9-one; and 4-benzylidene-7-hydroxy-1,2,3,4-tetrahydro-9H-xanthen-9-one.

EXAMPLE 20

By proceeding according to Examples 13 and 15 starting from hydroxy-1,2,3,9-tetrahydro-cyclopenta[b][1]benzopyran-9-one, the following compounds were prepared:

(3-benzylidene-1,2,3,9-tetrahydro-9-oxo-cyclopenta[b][1]benzopyran-6-yloxy)-oxoacetic acid, ethyl ester;

(3-benzylidene-1,2,3,9-tetrahydro-9-oxo-cyclopenta[b][1]benzopyran-7-yloxy)-oxoacetic acid, ethyl ester;

3-[(3-benzylidene-1,2,3,9-tetrahydro-9-oxo-cyclopenta[b][1]benzopyran-6-yloxy)-carbonyl]-propanoic acid;

3-[(3-benzylidene-1,2,3,9-tetrahydro-9-oxo-cyclopenta[b][1]benzopyran-7-yloxy)-carbonyl]-propanoic acid;

(Z)-3-[(3-benzylidene-1,2,3,9-tetrahydro-9-oxo-cyclopenta[b][1]benzopyran-6-yloxy)-carbonyl]-2-propenoic acid; and (Z)-3-[(3-benzylidene-1,2,3,9-tetrahydro-9-oxo-cyclopenta[b][1]benzopyran-7-yloxy)-carbonyl]-2-propenoic acid.

EXAMPLE 21

By proceeding according to Example 18 starting from hydroxy-1,2,3,9-tetrahydro-cyclopenta[b][1]benzopyran-9-one, the following compounds were prepared:

3-benzylidene-6-morpholinoacetoxy-1,2,3,9-tetrahydro-cyclopenta[b][1]benzopyran-9-one;

3-benzylidene-7-morpholinoacetoxy-1,2,3,9-tetrahydro-cyclopenta[b][1]benzopyran-9-one, m.p. 204°–206° C.;

3-benzylidene-6-piperidinoacetoxy-1,2,3,9-tetrahydro-cyclopenta[b][1]benzopyran-9-one;

3-benzylidene-7-piperidinoacetoxy-1,2,3,9-tetrahydro-cyclopenta[b][1]benzopyran-9-one;

3-benzylidene-6-[(4-methyl-piperazin-1-yl)-acetoxy]-1,2,3,9-tetrahydro-cyclopenta[b][1]benzopyran-9-one;

3-benzylidene-7-[(4-methyl-piperazin-1-yl)-acetoxy]-1,2,3,9-tetrahydro-cyclopenta[b][1]benzopyran-9-one; and 3-benzylidene-7-chloroacetoxy-1,2,3,9-tetrahydro-cyclopenta[b][1]benzopyran-9-one, m.p. 190°–204° C.(dec).

EXAMPLE 22

3-(4-nitro-benzylidene)-1,2,3,9-tetrahydro-9-oxo-cyclopenta[b][1]benzopyran-7-carboxylic acid, methyl ester (3.8 g), was reacted with $SnCl_2.2H_2O$ (11.5 g) in acetic acid (130 ml) and 37% HCl (26.5 ml) under stirring at 60° C. for 3 hours: after cooling the precipitate was filtered and washed with 2N HCl and water finely dispersed in 2N NaOH. The precipitate was filtered and washed with water until neutral to give 3-(4-amino-benzylidene)-1,2,3,9-tetrahydro-9-oxo-cyclopenta[b][1]benzopyran-7-carboxylic acid, methyl ester m.p. 265°–268° C. (2.9 g), which was treated with 37% HCl (60 ml) in acetic acid (120 ml) under stirring at 100° C. for 4 hours. After cooling the precipitate was filtered and then suspended under stirring in water containing $Na_2HPO_4$: the precipitate was filtered and washed with water to give 2.1 g of 3-(4-amino-benzylidene)-1,2,3,9tetrahydro-9-oxo-cyclopenta[b][1]benzopyran-7-carboxylic acid, m.p. 360° C. dec., NMR (DMSO $d_6$) δppm: 2.90 (m) (4H, C-1 and C-2 protons), 3.30 (bs) (2H, $NH_2$), 6.64 (d) (2H, C-3 and C-5 phenyl protons), 7.01 (bs) (1H=CH—), 7.31 (d) (2H, C-2 and C-6 phenyl protons, 7.69 (d) (1H, C-5 proton), 8.19 (dd) (1H, C-6 proton), 8.59 (d) (1H, C-8 proton).

EXAMPLE 23

3-(2-methyl-benzylidene)-1,2,3,9-tetrahydro-9-oxo-cyclopenta[b][1]benzopyran-7-carboxylic acid (2 g) was dissolved in the stoichiometric amount of 4N NaOH by heating at 80° C. After concentration in vacuo about to dryness and dilution of the residue with acetone (100 ml), the precipitate was filtered and washed with acetone: 1.85 g of 3-(2-methyl-benzylidene)-1,2,3,9-tetrahydro-9-oxo-cyclopenta[b][1]benzopyran-7-carboxylic acid, sodium salt, m.p. >300° C., were obtained.

By proceeding analogously the following compounds were obtained:
3-(4-ethoxy-benzylidene)-1,2,3,9-tetrahydro-9-oxo-cyclopenta[b][1]benzopyran-7-carboxylic acid, sodium salt;
3-(4-fluoro-benzylidene)-1,2,3,9-tetrahydro-9-oxo-cyclopenta[b][1]benzopyran-7-carboxylic acid, sodium salt;
3-benzylidene-1,2,3,9-tetrahydro-9-oxo-cyclopenta[b][1]benzopyran-7-carboxylic acid, sodium salt;
3-(2,3-dimethoxy-benzylidene)-1,2,3,9-tetrahydro-9-oxo-cyclopenta[b][1]benzopyran-7-carboxylic acid, sodium salt;
3-(4-chloro-benzylidene)-1,2,3,9-tetrahydro-9-oxo-cyclopenta[b][1]benzopyran-7-carboxylic acid, sodium salt; and
3-(2,6-dichloro-benzylidene)-1,2,3,9-tetrahydro-9-oxo-cyclopenta[b][1]benzopyran-7-carboxylic acid, sodium salt.

EXAMPLE 24

3-Benzylidene-6-hydroxy-1,2,3,9-tetrahydro-cyclopenta[b][1]benzopyran-9-one (1.5 g) was reacted with ethyl 2-bromo-acetate (1.67 g) in dimethylformamide (60 ml), in the presence of anhydrous $K_2CO_3$ (1.38 g), under stirring at room temperature for 3 hours. The reaction mixture was diluted with ice water containing $NaH_2PO_4$ and the precipitated product was filtered and washed with water: crystallization from $CH_2Cl_2$/methanol gave (3-benzylidene-1,2,3,9-tetrahydro-9-oxo-cyclopenta[b][1]benzopyran-6-yloxy)acetic acid, ethyl ester, m.p. 152°–154° C. (1.75 g), which was dissolved in dimethylformamide (22 ml) and treated with 2N NaOH (11.5 ml) at room temperature for 2 hours. The reaction mixture was acidified with 2N HCl and then diluted with ice water: the precipitated product was filtered and washed with water until neutral. Crystallization from $CHCl_3$/ethanol gave 1.4 g of (3-benzylidene-1,2,3,9-tetrahydro-9-oxo-cyclopenta[b][1]benzopyran-6-yloxy)-acetic acid, m.p. 277°–279° C.

By proceeding analogously the following compounds were prepared:
[3-(2-methyl-benzylidene)-1,2,3,9-tetrahydro-9-oxo-cyclopenta[b][1]benzopyran-6-yloxy]-acetic acid;
3-(3-benzylidene-1,2,3,9-tetrahydro-9-oxo-cyclopenta[b][1]benzopyran-6-yloxy)-propanoic acid;
[3-(3-methyl-benzylidene)-1,2,3,9-tetrahydro-9-oxo-cyclopenta[b][1]benzopyran-6-yloxy]-acetic acid;
[3-(4-methyl-benzylidene)-1,2,3,9-tetrahydro-9-oxo-cyclopenta[b][1]benzopyran-6-yloxy]-acetic acid;
[3-(2,5-dimethyl-benzylidene)-1,2,3,9-tetrahydro-9-oxo-cyclopenta[b][1]benzopyran-6-yloxy]-acetic acid;
[3-(2-methoxy-benzylidene)-1,2,3,9-tetrahydro-9-oxo-cyclopenta[b][1]benzopyran-6-yloxy]-acetic acid;
[3-(3-methoxy-benzylidene)-1,2,3,9-tetrahydro-9-oxo-cyclopenta[b][1]benzopyran-6-yloxy]-acetic acid;
[3-(4-methoxy-benzylidene)-1,2,3,9-tetrahydro-9-oxo-cyclopenta[b][1]benzopyran-6-yloxy]-acetic acid;
[3-(2-ethoxy-benzylidene)-1,2,3,9-tetrahydro-9-oxo-cyclopenta[b][1]benzopyran-6-yloxy]-acetic acid;
[3-(3-ethoxy-benzylidene)-1,2,3,9-tetrahydro-9-oxo-cyclopenta[b][1]benzopyran-6-yloxy]-acetic acid;
[3-(4-ethoxy-benzylidene)-1,2,3,9-tetrahydro-9-oxo-cyclopenta[b][1]benzopyran-6-yloxy]-acetic acid;
[3-(2,3-dimethoxy-benzylidene)-1,2,3,9-tetrahydro-9-oxo-cyclopenta[b][1]benzopyran-6-yloxy]-acetic acid;
[3-(2,5-dimethoxy-benzylidene)-1,2,3,9-tetrahydro-9-oxo-cyclopenta[b][1]benzopyran-6-yloxy]-acetic acid;
[3-(2-methoxy-3-ethoxy-benzylidene)-1,2,3,9-tetrahydro-9-oxo-cyclopenta[b][1]benzopyran-6-yloxy]-acetic acid;
[3-(2-chloro-benzylidene)-1,2,3,9-tetrahydro-9-oxo-cyclopenta[b][1]benzopyran-6-yloxy]-acetic acid;
[3-(3-chloro-benzylidene)-1,2,3,9-tetrahydro-9-oxo-cyclopenta[b][1]benzopyran-6-yloxy]-acetic acid;
[3-(4-chloro-benzylidene)-1,2,3,9-tetrahydro-9-oxo-cyclopenta[b][1]benzopyran-6-yloxy]-acetic acid;
[3-(2,6-dichloro-benzylidene)-1,2,3,9-tetrahydro-9-oxo-cyclopenta[b][1]benzopyran-6-yloxy]-acetic acid;
[3-(4-fluoro-benzylidene)-1,2,3,9-tetrahydro-9-oxo-cyclopenta[b][1]benzopyran-6-yloxy]-acetic acid;
3-[3-(2-methyl-benzylidene)-1,2,3,9-tetrahydro-9-oxo-cyclopenta[b][1]benzopyran-6-yloxy]-propanoic acid;
N-(3-benzylidene-1,2,3,9-tetrahydro-9-oxo-cyclopenta[b][1]benzopyran-6-yl)-amino-acetic acid;
N-[3-(2-methyl-benzylidene)-1,2,3,9-tetrahydro-9-oxo-cyclopenta[b][1]benzopyran-6-yl]-amino-acetic acid;
3-N-(3-benzylidene-1,2,3,9-tetrahydro-9-oxo-cyclopenta[b][1]benzopyran-6-yl)-amino-propanoic acid; and
3-N-[3-(2-methyl-benzylidene)-1,2,3,9-tetrahydro-9-oxo-cyclopenta[b][1]benzopyran-6-yl]-amino-propanoic acid.

EXAMPLE 25

3-Benzylidene-6-hydroxy-1,2,3,9-tetrahydro-cyclopenta[b][1]benzopyran-9-one (1.2 g) was reacted with 4-(2-chloro-ethyl)-morpholine (1.15 g) in dimethylformamide (50 ml), in the presence of anhydrous K₂CO₃ (1.7 g), under stirring for 4 hours at room temperature and then for 1 hour at 70° C. The reaction mixture was diluted with ice water containing NaH₂PO₄ and the precipitated product was filtered and washed with water. Crystallization from CH₂Cl₂/isopropyl alcohol gave 0.9 g of 3-benzylidene-6-(2-morpholino-ethoxy)-1,2,3,9-tetrahydro-cyclopenta[b][1]benzopyran-9-one, m.p. 167°–169° C.

By proceeding analogously the following compounds were prepared:

3-(2-methyl-benzylidene)-6-(2-morpholino-ethoxy)-1,2,3,9-tetrahydro-cyclopenta[b][1]benzopyran-9-one;

3-benzylidene-6-(2-piperidino-ethoxy)-1,2,3,9-tetrahydro-cyclopenta[b][1]benzopyran-9-one;

3-benzylidene-6-[2-(pyrrolidin-1-yl)-ethoxy]-1,2,3,9-tetrahydro-cyclopenta[b][1]benzopyran-9-one;

3-benzylidene-6-N-(2-morpholino-ethyl)-amino-1,2,3,9-tetrahydro-cyclopenta[b][1]benzopyran-9-one;

3-(2-methyl-benzylidene)-6-N-(2-morpholino-ethyl)-amino-1,2,3,9-tetrahydro-cyclopenta[b][1]benzopyran-9-one;

3-benzylidene-6-N-(2-piperidino-ethyl)-amino-1,2,3,9-tetrahydro-cyclopenta[b][1]benzopyran-9-one; and 3-benzylidene-6-N-[2-(pyrrolidin-1-yl)-ethyl]-amino-1,2,3,9-tetrahydro-cyclopenta[b][1]benzopyran-9-one.

3-benzylidene-7-[2-(N,N-dimethyl-amino)-ethoxy]-1,2,3,4-tetrahydro-9H-xanthen-9-one;

3-benzylidene-6-[2-(N,N-diethyl-amino)-ethoxy]-1,2,3,9-tetrahydro-cyclopenta[b][1]benzopyran-9-one;

3-(2-methyl-benzylidene)-6-[2-(N,N-diethyl-amino)-ethoxy]-1,2,3,9-tetrahydro-cyclopenta[b][1]benzopyran-9-one;

3-benzylidene-6-[2-(N,N-dimethyl-amino)-ethoxy]-1,2,3,9-tetrahydro-cyclopenta[b][1]benzopyran-9-one;

3-benzylidene-7-[2-(N,N-diethyl-amino)-ethoxy]-1,2,3,9-tetrahydro-cyclopenta[b][1]benzopyran-9-one;

3-(2-methyl-benzylidene)-7-[2-(N,N-diethyl-amino)-ethoxy]-1,2,3,9-tetrahydro-cyclopenta[b][1]benzopyran-9-one;

3-benzylidene-7-[2-(N,N-dimethyl-amino)-ethoxy]-1,2,3,9-tetrahydro-cyclopenta[b][1]benzopyran-9-one;

4-benzylidene-6-[2-(N,N-diethyl-amino)-ethoxy]-1,2,3,4-tetrahydro-9H-xanthen-9-one;

4-benzylidene-7-[2-(N,N-diethyl-amino)-ethoxy]-1,2,3,4-tetrahydro-9H-xanthen-9-one; and 4-(2-methyl-benzylidene)-7-[2-(N,N-diethyl-amino)-ethoxy]-1,2,3,4-tetrahydro-9H-xanthen-9-one.

EXAMPLE 26

Tablets, each weighing 200 mg and containing 100 mg of the active substances were manufactured as follows: Compositions (for 10,000 tablets)

3-(2-methyl-benzylidene)-1,2,3,9-tetrahydro-9-oxo-cyclopenta[b][1]benzopyran-7-carboxylic acid: 1000 g Lactose: 710 g
Corn starch: 237.5 g
Talc powder: 37.5 g
Magnesium stearate: 15 g 3-(2-methyl-benzylidene)-1,2,3,9-tetrahydro-9-oxo-cyclopenta[b][1]benzopyran-7-carboxylic acid, lactose and a half of the corn starch were mixed; the mixture was then forced through a sieve of 0.5 mm openings. Corn starch (18 g) was suspended in warm water (180 ml). The resulting paste was used to granulate the powder. The granules were dried, comminuted on a sieve size 1.4 mm, then the remaining quantity of starch, talc and magnesium stearate was added, carefully mixed and processed into tablets using punches of 8 mm diameter.

We claim:

1. A compound of formula (I)

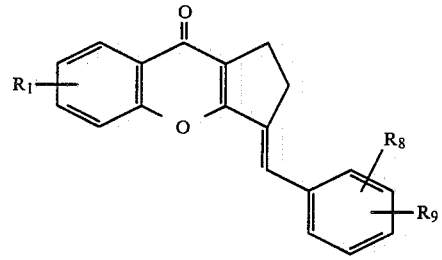

wherein
$R_1$ is amino, hydroxy, carboxy, $C_1$–$C_4$ alkoxycarbonyl unsubstituted or substituted by di($C_1$–$C_4$)alkylamino, —NHCOCOOR, —NHCOCH═CH—COOR, wherein R is hydrogen or $C_1$–$C_4$ alkyl, —NHCO(CH₂)$_p$—COOR or —O—(CH₂)$_p$—COOR, wherein p is 1, 2 or 3 and R is as defined above;
each of $R_8$ and $R_9$ independently is hydrogen, halogen, $C_1$–$C_4$ alkyl, $C_1$–$C_4$ alkoxy, di($C_1$–$C_4$) alkylamino or $R_8$ and $R_9$, being adjacent, taken together form a methylenedioxy group; or a pharmaceutically acceptable salt thereof.

2. A compound of formula (I)

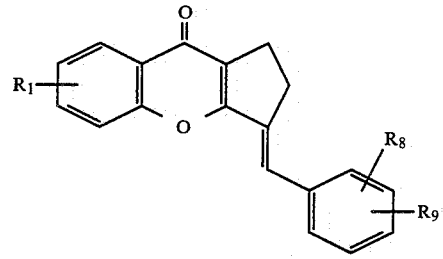

wherein
$R_1$ is amino, hydroxy, carboxy, or $C_1$–$C_4$ alkoxy-carbonyl unsubstituted or substituted by di($C_1$–$C_4$)alkylamino;
each of $R_8$ and $R_9$ independently is hydrogen, halogen, $C_1$–$C_4$ alkyl, $C_1$–$C_4$ alkoxy, or di($C_1$–$C_4$)alkylamino; or a pharmaceutically acceptable salt thereof.

3. A compound selected from the group consisting of:
3-benzylidene-1,2,3,9-tetrahydro-9-oxo-cyclopenta[b][1]benzopyran-7-carboxylic acid;
3-(2-methyl-benzylidene)-1,2,3,9-tetrahydro-9-oxo-cyclopenta[b][1]benzopyran-7-carboxylic acid;
3-(3-methoxy-benzylidene)-1,2,3,9-tetrahydro-9-oxo-cyclopenta[b][1]benzopyran-7-carboxylic acid;
3-(4-methoxy-benzylidene)-1,2,3,9-tetrahydro-9-oxo-cyclopenta[b][1]benzopyran-7-carboxylic acid;
3-(2,3-dimethoxy-benzylidene)-1,2,3,9-tetrahydro-9-oxo-cyclopenta[b][1]benzopyran-7-carboxylic acid;

3-(2,5-dimethoxy-benzylidene)-1,2,3,9-tetrahydro-9-oxo-cyclopenta[b][1]benzopyran-7-carboxylic acid;
3-(4-fluoro-benzylidene)-1,2,3,9-tetrahydro-9-oxo-cyclopenta[b][1]benzopyran-7-carboxylic acid;
3-(2-chloro-benzylidene)-1,2,3,9-tetrahydro-9-oxo-cyclopenta[b][1]benzopyran-7-carboxylic acid;
3-(3-chloro-benzylidene)-1,2,3,9-tetrahydro-9-oxo-cyclopenta[b][1]benzopyran-7-carboxylic acid;
3-(4-chloro-benzylidene)-1,2,3,9-tetrahydro-9-oxo-cyclopenta[b][1]benzopyran-7-carboxylic acid;
3-(2-ethoxy-benzylidene)-1,2,3,9-tetrahydro-9-oxo-cyclopenta[b][1]benzopyran-7-carboxylic acid;
3-(3-ethoxy-benzylidene)-1,2,3,9-tetrahydro-9-oxo-cyclopenta[b][1]benzopyran-7-carboxylic acid;
3-(4-ethoxy-benzylidene)-1,2,3,9-tetrahydro-9-oxo-cyclopenta[b][1]benzopyran-7-carboxylic acid;
3-(2,5-dimethyl-benzylidene)-1,2,3,9-tetrahydro-9-oxo-cyclopenta[b][1]benzopyran-7-carboxylic acid;
3-(2-methoxy-3-ethoxy-benzylidene)-1,2,3,9-tetrahydro-9-oxo-cyclopenta[b][1]benzopyran-7-carboxlic acid;
N-(3-benzylidene-1,2,3,9-tetrahydro-9-oxo-cyclopenta[b][1]benzopyran-6-yl)-amino-oxoacetic acid;
N-[3-(2-methyl-benzylidene)-1,2,3,9-tetrahydro-9-oxo-cyclopenta[b][1]benzopyran-6-yl]-amino-oxoacetic acid;
N-[3-(2-chloro-benzylidene)-1,2,3,9-tetrahydro-9-oxo-cyclopenta[b][1]benzopyran-6-yl]-amino-oxoacetic acid;
N-[3-(4-chloro-benzylidene)-1,2,3,9-tetrahydro-9-oxo-cyclopenta[b][1]benzopyran-6-yl]-amino-oxoacetic acid;
N-[3-(4-fluoro-benzylidene)-1,2,3,9-tetrahydro-9-oxo-cyclopenta[b][1]benzopyran-6-yl]-amino-oxoacetic acid;
N-[3-(4-ethoxy-benzylidene)-1,2,3,9-tetrahydro-9-oxo-cyclopenta[b][1]benzopyran-6-yl]-amino-oxoacetic acid;
N-[3-(4-methoxy-benzylidene)-1,2,3,9-tetrahydro-9-oxo-cyclopenta[b][1]benzopyran-6-yl]-amino-oxoacetic acid;
N-[3-(2,5-dimethyl-benzylidene)-1,2,3,9-tetrahydro-9-oxo-cyclopenta[b][1]benzopyran-6-yl]-amino-oxoacetic acid;
N-[3-(2,3-dimethoxy-benzylidene)-1,2,3,9-tetrahydro-9-oxo-cyclopenta[b][1]benzopyran-6-yl]-amino-oxoacetic acid;
N-[3-(2,6-dichloro-benzylidene)-1,2,3,9-tetrahydro-9-oxo-cyclopenta[b][1]benzopyran-6-yl]-amino-oxoacetic acid;
N-[3-(3-chloro-benzylidene-1,2,3,9-tetrahydro-9-oxo-cyclopenta[b][1]benzopyran-6-yl]-amino-oxoacetic acid;
(3-benzylidene-1,2,3,9-tetrahydro-9-oxo-cyclopenta[b][1]benzopyran-6-yloxy)-acetic acid;
(E)-3-[N-(3-benzylidene-1,2,3,9-tetrahydro-9-oxo-cyclopenta[b][1]benzopyran-6-yl)-aminocarbonyl]-2-propenoic acid;
(Z)-3-[N-(3-benzylidene-1,2,3,9-tetrahydro-9-oxo-cyclopenta[b][1]benzopyran-6-yl)-aminocarbonyl]-2-propenoic acid;
or a pharmaceutically acceptable salt thereof.

4. An anti-allery composition comprising an anti-allergic effective amount of a compound of claim 1 and a pharmaceutically acceptable carrier.

5. A method of producing an anti-allergic effect in a patient in need of such affect, said method comprising administering to said patient an anti-allergic effective amount of a compound of the formula:

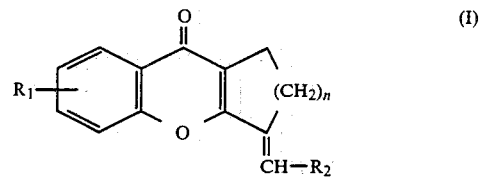

wherein
n is 1 or 2;
$R_1$ is
(a) hydrogen, halogen or $C_1$–$C_6$ alkyl;
(b) cyano, aminocarbonyl, carboxy or a $C_1$–$C_6$ alkoxycarbonyl group unsubstituted or substituted by a di($C_1$–$C_6$)alkylamino group;
(c) nitro, amino;
(d) a

group, wherein $R_3$ is hydrogen or $C_1$–$C_6$ alkyl and $R_4$ is:
(a') formyl, $C_2$–$C_6$ alkanoyl or $C_1$–$C_6$ alkyl, wherein the alkyl is unsubstituted or substituted by one or two substituents chosen from hydroxy and phenyl;
(b') a—(CO)$_m$—A—$R_5$ group, wherein m is zero or 1; A completes a single bond, or is a phenylene moiety, or it is a branched or straight $C_1$–$C_6$ alkylene or $C_2$–$C_6$ alkenylene chain and $R_5$ is:
(a″) carboxy or $C_1$–$C_6$ alkoxycarbonyl, unsubstituted or substituted by a di-($C_1$–$C_6$)alkylamino group; or
(b″) halomethyl or

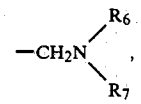

wherein each of $R_6$ and $R_7$ is independently hydrogen or $C_1$–$C_6$ alkyl
(e) hydroxy or a —$OR_4$ group, wherein $R_4$ is as defined above;
$R_2$ is a group of the formula

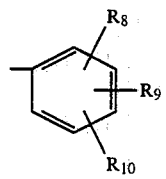

wherein each of $R_8$, $R_9$ and $R_{10}$ is independently hydrogen; halogen; $C_1$–$C_6$ alkyl; hydroxy; $C_1$–$C_6$ alkoxy; $C_3$–$C_4$ alkenyloxy; formyloxy; $C_2$–$C_6$ alkanoyloxy; carboxy; $C_1$–$C_6$ alkoxycarbonyl; nitro; or a group

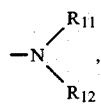
wherein each of $R_{11}$ and $R_{12}$ independently represents hydrogen, $C_1$–$C_6$ alkyl, formyl or $C_2$–$C_6$ alkanoyl; or any two adjacent $R_8$, $R_9$ and $R_{10}$ groups, taken together, form a $C_1$–$C_3$ alkylenedioxy group, or a pharmaceutically acceptable salt thereof, and wherein, when n is 1 and, at the same time, $R_2$ is unsubstituted phenyl, $R_1$ is other then hydrogen.
* * * * *